United States Patent [19]

Bini

[11] Patent Number: 5,922,322
[45] Date of Patent: *Jul. 13, 1999

[54] FIBRIN(OGEN) DEGRADATION AND CLOT LYSIS BY FIBRINOLYTIC MATRIX METALLOPROTEINASE

[75] Inventor: Alessandra Bini, New York, N.Y.

[73] Assignee: New York Blood Center, Inc., New York, N.Y.

[ * ] Notice: This patent is subject to a terminal disclaimer.

[21] Appl. No.: 08/765,815

[22] Filed: Jan. 17, 1997

Related U.S. Application Data

[63] Continuation-in-part of application No. 08/446,887, May 17, 1995, Pat. No. 5,830,468.

[51] Int. Cl.$^6$ .............................. C12N 9/50; C12N 15/00
[52] U.S. Cl. .................... 424/94.67; 424/94.63; 424/94.1; 514/2; 435/212; 435/226; 604/280
[58] Field of Search ................................ 424/94.1, 94.63, 424/94.67; 514/2; 435/212, 226; 604/280

[56] References Cited

U.S. PATENT DOCUMENTS

| | | | |
|---|---|---|---|
| 4,378,803 | 4/1983 | Takagi et al. | 604/280 |
| 4,610,879 | 9/1986 | Markland, Jr. et al. | 424/94.67 |
| 4,813,538 | 3/1989 | Blackman | 206/210 |
| 5,130,143 | 7/1992 | Strickland et al. | 424/94.64 |
| 5,185,001 | 2/1993 | Galanakis | 604/5 |
| 5,202,121 | 4/1993 | Pohl et al. | 424/94.64 |
| 5,260,059 | 11/1993 | Acott et al. | 424/94.67 |
| 5,260,060 | 11/1993 | Markland, Jr. et al. | 424/94.67 |
| 5,324,634 | 6/1994 | Zucker | 435/7.23 |

OTHER PUBLICATIONS

Francis CW, and Marder VJ, "Physiologic regulation and pathologic disorders of fibrinolysis", Chapter 54 in *Hemostasis and Thrombosis: Basic Principles and Clinical Practice*, 3rd. ed., Colman RW, Hirsh J, Marder VJ, and Salzman EW, eds., JB Lippincott Co, Philadelphia (1994).

Collen D, "On the regulation and control of fibrinolysis", *Thromb Haemost* 43:77–89 (1980).

Collen D, and Lijnen HR, "Basic and clinical aspects of fibrinolysis and thrombolysis" *Blood* 3114–24 (1991).

Murphy G. Atkinson S, Ward R, Gavrilovic J, and Reynolds JJ, "The role of plasminogen activators in the regulation of connective tissue metalloproteinases", *Ann NY Acad Sci*, 667:1–12 (1992).

Singer et al., "VDIPEN, A Metalloproteinase–generated Neoepitope, Is Induced and Immunolocalized in Articular Cartilage during Inflammatory Arthritis", *Journal of Clinical Investigation, Inc.*, 95:2178–2186 (1995).

Martin GV, Kennedy JW, and Marder VJ, "Thrombolytic therapy for coronary artery disease", Chapter 73 in *Hemostasis and Thrombosis: Basic Principles and Clinical Practice*, 3rd ed., Colman RW, Hirsh J, Marder VJ, and Salzman EW, eds., JB Lippincott Co, Phildelphia (1994).

Glick, BR and Pasternak JJ, "Molecular Biotechnology: Principles and Applications of Recombinant DNA", Chapter 17, pp. 403–420 (1994).

Collen D, "Biological properties of plasminogen activators", Chapter 1 in Sobel BE, Collen D, and Grossbard EB, eds., *Tissue Plasminogen Activator in Thrombolytic therapy*, Marcel Dekker, Inc., New York (1987).

Lee SW, Kahn ML, and Dichek DA, "Control of clot lysis by gene transfer", *Trends Cardiovasc Med* 3:61–66 (1993).

Purves L, Purves M, and Brandt W, "Cleavage of fibrin–derived D–dimer into monomers by endopeptidase from puff adder venom (*Bitis arietans*) acting at cross–linked sites of the γ–chain. Sequence of carboxy–terminal cyanogen bromide γ–chain fragments", *Biochemistry* 26:4640–46 (1987).

Retzios AD, and Markland FS Jr, "Purification, characterization, and fibrinogen cleavage sites of three fibrinolytic enzymes from the venom of *Crotalus basiliscus basiliscus*", *Biochemistry* 31:4547–57 (1992).

Sanchez EF, Magalhes A, Mandelbaum FR, and Diniz CR, "Purification and characterization of the hemorrhagic factor II from the venom of the Bushmaster snake (*Lachesis muta muta*)", *Biochem Biophys Acta* 1074:347–56 (1991).

Nagase H, Barrett, AJ, and Woessner JF Jr, "Nomenclature and glossary of the matrix metalloproteinases", *Matrix*, Supplement No. 1:421–24 (1992).

Zavalova LL, Kuzina EV, Levina NB, and Baskova IP, "Monomerization of fragment DD by destabilase from the medicinal leech does not alter the N–terminal sequence of the γ–chain", *Thrombosis Res* 71:241–44 (1993).

Budzynski AZ, "Interaction of hementin with fibrinogen and fibrin", *Blood Coagulation and Fibrinolysis* 2:149–52 (1991).

Loewy, AG, Santer UV, Wieczorek M, Blodgett JK, Jones SW, and Cheronis JC, "Purification and characterization of a novel zinc–proteinase from cultures of *Aeromonas hydrophila*", *J. Biol Chem* 268:9071–78 (1993).

(List continued on next page.)

*Primary Examiner*—Elizabeth Kemmerer
*Attorney, Agent, or Firm*—Hoffman & Baron, LLP

[57] ABSTRACT

The invention provides a method of causing degradation of fibrin(ogen) (i.e., fibrin, fibrinogen, and related substances) by means of a fibrinolytic metalloproteinase, preferably an endogenous metalloproteinase such as MMP-3. The method of the invention can be performed in vitro to provide diagnostic information characterizing fibrin(ogen) and fibrinolytic physiology. The method can also be performed in vivo as a method of thrombolytic therapy in which a fibrinolytic metalloproteinase is administered to a subject to degrade thrombus in situ. The endogenous fibrinolytic metalloproteinase can be administered in conjunction with other active agents, preferably with agents having thrombolytic activity to improve thrombolytic and fibrinolytic therapy. The invention further provides compositions containing a fibrinolytic metalloproteinase for the performance of fibrinolytic or thrombolytic procedures. Also provided are kits which include a fibrinolytic metalloproteinase for performing fibrinolytic or thrombolytic procedures.

30 Claims, 9 Drawing Sheets

OTHER PUBLICATIONS

Cawston T, "Metalloproteinase inhibitors—Crystal gazing for a future therapy", *Br J. Rheumtol* 30:242–44 (1991).

Kleiner DE Jr, and Stetler–Stevenson WG, "Structural biochemistry and activation of matrix metalloproteinase", *Curr Opin Cell Biol* 5:891–97 (1993).

Matrisian LM, "The matrix–degrading metalloproteinases", *BipoEssays* 14:455–63 (1992).

Nagase H, Enghild JJ, Suzuki K, and Salvesen G, "Stepwise activation mechanisms of the precursor of matrix metalloproteinase 3 (stromelysin) by proteases and (4–aminophenyl)mercuric acetate", *Biochemistry* 29:5783–89 (1990).

Nagase H, Ogota Y, Suzuki K, Enghild JJ, and Salvesen G, "Substrate specificities and activation mechanisms of matrix metalloproteinases", *Biochem Soc Trans* 19:715–18 (1991).

Henney AM, Wakeley PR, Davies MJ, Foster K, Hembry R, Murphy G, and Humphries S, "Localization of stromelysis gene expression in atherosclerotic plaques by in situ hybridization", *Proc Natl Acad Sci USA* 88:8154–58 (1991).

Galis ZS, Sukhova GK, Lark MW, and Libby P, "Increased expression of matrix metalloproteinases and matrix degrading activity in vulnerable regions of human atherosclerotic plaques", *J. Clin Invest* 94:2493–2503 (1994).

Doolittle RF, "Fibrinogen and fibrin", in Bloom AL, and Thomas DP, eds., *Hemostasis and Thrombosis* Churchill Livingston, Edinburgh, New York (1987).

Fu Y, and Grieninger G, "Fib$_{420}$: A normal human variant of fibrinogen with two extended α chains", *Proc Natl Acad Sci USA* 91:2625–28 (1994).

Gabriel DA, Muga K, and Boothroyd EM, "The effect of fibrin structure on fibrinolysis", *J. Biol. Chem* 267:24259–63 (1993).

Kudryk BJ, Grossman ZD, McAfee JG, and Rosebrough SF, "Monoclonal antibodies as probes for fibrin(ogen) proteolysis", Chapter 19 in *Monoclonal Antibodies in Immunoscintigraphy*, Chatal J–F, ed., CRC Press, Boca Raton (1989).

Bini A, Mesa–Tejada RM, Fenoglio J, Kudryk B, and Kaplan KL, "Immunohistochemical Characterization of Fibrin(ogen)–Related Antigens in Human Tissues Using Monoclonal Antibodies", *Laboratory Investigation*, 60–814–821 (1989).

Bini A, Callender S, Pocyk R, Blombäck B, and Kudryk BJ, "Flow and antibody binding properties of hydrated fibrins prepared from plasma, platelet rich plasma and whole blood", *Thrombosis Res* 76:145–56 (1994).

Okada Y, Nagase H, and Harris ED, Jr., "A metalloproteinase from human rheumatoid synovial fibroblasts that digests connective tissue matrix components", *J Biol Chem* 261:14245–55 (1986).

Tyagi SC, Ratajska A, and Weber LT, "Myocardial matrix metalloproteinase(s):localization and activation", *mol. Cell Biochem,* 126:49–59 (1993).

Bini A and Kudryk BJ, "Fibrin and Its Derivatives in the Normal and Diseased Vessel Wall", in *Plasminogen Activation in Fibrinolysis, in Tissue Remodeling and in Development, Ann NY Acad Sci,* 677:112–126, (1992).

Bini A, Fenoglio J, Sobel J, Owen J, Fejgl M, and Kaplan KL, "Immunochemical Characterization of Fibrinogen, Fibrin I, and Fibrin II in Human Thrombi and Atherosclerotic Lesions", *Blood,* 69:1038–1045 (1987).

Bini A, Fenoglio J, Mesa–Tejada RM, Kudryk B, and Kaplan KL, "Identification and Distribution of Fibrinogen, Fibrin, and Fibrin(ogen) Degradation Products in Atherosclerosis, Use of Monoclonal Antibodies", *Arteriosclerosis,* 9:109–121 (1989).

D-dimer (186 kDa)-
D (93 kDa)-

1  2  3  4  5

γ-dimer (76 kDa)-

β (43 kDa)-
γ (38 kDa)-

α (12 kDa)-

1  2  3  4  5

FIBRIN(OGEN) DEGRADATION AND CLOT LYSIS BY FIBRINOLYTIC MATRIX METALLOPROTEINASE

This is a continuation-in-part of application Ser. No. 08/446,887, filed on May 17, 1995, now U.S. Pat. No. 5,830,468, the entire disclosure of which is incorporated herein by reference.

BACKGROUND OF THE INVENTION

This invention relates to a method of enzyme-mediated breakdown of fibrinogen and fibrin. More particularly, the invention relates to a method for degrading fibrinogen and causing lysis of fibrin clots through mediation by a fibrinolytic matrix metalloproteinase. The invention further relates to the use of fibrinolytic metalloproteinase as an antithrombotic to reconstruct stenotic vessels and remove fibrin deposits.

The clotting of blood is part of the body's natural response to injury or trauma. Blood clot formation derives from a series of events called the coagulation cascade, in which the final steps involve the formation of the enzyme thrombin. Thrombin converts circulating fibrinogen into fibrin, a mesh-like structure which forms the insoluble framework of the blood clot. As a part of hemostasis, clot formation is often a life-saving process in response to trauma and serves to arrest the flow of blood from severed vasculature.

The life-saving process of clot production in response to an injury can become life-threatening when it occurs at inappropriate places in the body. For example, a clot can obstruct a blood vessel and stop the supply of blood to an organ or other body part. In addition, the deposition of fibrin contributes to partial or complete stenosis of blood vessels, resulting in chronic diminution of blood flow. Equally life-threatening are clots that become detached from their original sites and flow through the circulatory system causing blockages at remote sites. Such clots are known as embolisms. Indeed, pathologies of blood coagulation, such as heart attacks, strokes, and the like, have been estimated to account for approximately fifty percent of all hospital deaths.

The formation of fibrin during inflammation, tissue repair, or hemostasis, plays only a temporary role and must be removed when normal tissue structure and function is restored. Thus, a fibrin clot that forms quickly to stop hemorrhage in an injured blood vessel is remodeled and then removed to restore normal blood flow as healing occurs. The system responsible for fibrin breakdown and clot removal is the fibrinolytic system. Action of the fibrinolytic system is tightly coordinated through the interaction of activators, zymogens, enzymes, as well as through inhibitors of each of these components, to provide focused local activation at sites of fibrin deposition (Francis et al. 1994; Collen 1980; Collen et al. 1991).

The principal mediator of fibrinolysis is plasmin, a trypsin-like endopeptidase which cleaves fibrin to dissolve clots and to permit injured tissues to regenerate. Plasmin has also been demonstrated to play a role in degrading proteins involved in cell-cell and cell-matrix interactions, as well as in activating other tissue remodeling enzymes such as matrix metalloproteinases (Murphy et al. 1992). In turn, control of plasmin activity, as well as these other extracellular events, is principally mediated by plasminogen activators, which convert the inactive zymogen plasminogen to the active enzyme plasmin.

In clinical settings it is commonly desirable to activate or potentiate the fibrinolytic system. This is particularly necessary in cases of myocardial infarction in which coronary arteries become occluded and require recanalization. Catheterization has proven somewhat effective in such recanalization, but pharmacologic agents are desired to supplement or replace such invasive procedures to inhibit reocclusion. The study of the intricate system of thrombolysis and fibrinolysis has been a rapidly growing field, which has resulted in the development of a new generation of thrombolytic agents.

Previous therapeutic treatments for dissolving life-threatening clots have included injecting into the blood system various enzymes which are known to break down fibrin. (Collen 1996) The problems with these treatments has been that the enzymes were not site-specific, and, therefore, would do more than just cause dissolution of the clot. In addition, these enzymes interfere with and destroy many vital protein interactions that serve to keep the body from bleeding excessively due to the many minor injuries it receives on a daily basis. Destruction of these safeguards by such enzymes can lead to serious hemorrhage and other potentially fatal complications.

Currently, the best known therapeutic agents for inducing or enhancing thrombolysis are compounds which cause the activation of plasminogen, the so-called "plasminogen activator" (Brakman et al. 1992). These compounds cause the hydrolysis of the arg560-val561 peptide bond in plasminogen. This hydrolysis yields the active two-chain serine protease, plasmin. A number of such plasminogen activators are known, including serine proteases such as urokinase plasminogen activator (u-PA), tissue-type plasminogen activator (t-PA), streptokinase (a non-enzyme protein) and staphylokinase. Of these, streptokinase is the most widely used therapeutic thrombolytic agent. However, while streptokinase and the other plasminogen activators have proven helpful in recanalization of coronary arteries, their ability to improve mortality is not devoid of side effects and their use still requires stringent control conditions to achieve success in a high percentage of cases (Martin et al. 1994). In addition, the use of such compounds can cause bleeding complications in susceptible individuals. On the other hand, one of the drawbacks of the use of t-PA in clinical trials has been the early reformation of the clot after it has been dissolved, resulting in thrombotic reocclusion in some patients.

Numerous studies have documented the ability of t-PA to initiate or potentiate thrombolytic phenomena (Sobel et al. 1987). As a result, t-PA, specifically its recombinant form, rt-PA, is becoming more popular as a thrombolytic pharmaceutical. Nonetheless, rt-PA does suffer from serious limitations, including extremely high dosage cost, and variable efficacy. In addition, specific rapid-acting inhibitors of t-PA have been identified in human plasma and other fluids (Collen et al. 1987). A further approach to t-PA involves the potential use of gene transfer of and expression of recombinant t-PA in endothelial cells (Lee et al. 1993). This procedure is exceedingly complex and is not likely to be practical as a thrombolytic treatment in the near future.

Enzymes other than plasmin are also known which can degrade fibrin(ogen) to different extents. For example, endogenous leukocyte proteases (Bilezikian et al. 1977; Plow et al. 1975), later identified as elastase and cathepsin-G (Gramse et al. 1978; Plow 1980; Plow et al. 1982), can partially degrade fibrin(ogen). Exogenous enzymes are also known which degrade fibrin. Such enzymes include hemolytic enzymes collected from the venom of certain snakes, e.g., the families crotalidae and viperidae (Purves et al. 1987; Retzios et al. 1992; Sanchez et al. 1991). Fibrinolytic enzymes isolated from snakes can be grouped into two different classes (Guan et al. 1991). Those enzymes that preferentially degrade the Aα-chain of fibrinogen and also the α- and β-chains of fibrin are zinc metalloproteases (Guan et al. 1991) and all can be inhibited by EDTA. Enzymes in the second class are serine proteinases, and exhibit specificity for the β-chain of fibrin (Guan et al. 1991). An endopeptidase from puff adder venom (*Bitis arietans*) can cleave at the γ-chain cross-linking site and thereby cleave Fragment D-dimer into a D-like monomer (Purves et al. 1987). Fibrinolytic enzymes have also been obtained from leeches (Zavalova et al. 1993; Budzynski 1991), as well as from the growth medium of a bacterium (*Aeromonas hydrophila*) which was recovered from leech intestinal tract (Loewy et al. 1993).

Endogenous matrix metalloproteinases (MMPs) or "matrixins" include three classes of enzymes: collagenases, gelatinases, and stromelysins. MMPs are known to have the capacity to degrade a number of proteins and proteoglycans which are associated with the extracellular matrix (ECM) of connective tissue. They have been shown to break down a number of proteins including collagen (Types I–IV, VII and X), laminin, fibronectin, elastin and proteoglycans. MMPs have also been identified in leukocytes (Welgus et al. 1990). It has been shown that MMP-2 and MMP-9 possess elastase activity (Senior et al. 1991), to which some of the complex proteolytic activity, initially observed in granulocytes, could be attributed (Sterrenberg et al. 1983). MMPs participate in the remodeling of tissues in physiological processes such as morphogenesis and embryonic development, as well as in the pathophysiology of wound healing, tumor invasion, and arthritis (Matrisian 1992; Nagase et al. 1991; Woessner 1991; Werb et al. 1992).

The expression of MMPs and their inhibitors is under extensive and varied molecular and cellular control (Kleiner et al. 1993; Matrisian 1992; Woessner 1991). Known regulating factors include hormones, cytokines, proto-oncogenes, steroids, and growth factors. MMPs are blocked by specific inhibitors called "tissue inhibitors of metalloproteinases" (TIMPs) that can block the activity of each member of the family. An enzyme inhibitor complex is formed and no turnover of connective tissue takes place if the MMPs are present in excess. The main focus of research on ECM has been to limit ECM degradation by MMPs to interrupt or interfere with the progression of disease states. Several groups of investigators are making small molecules that could inhibit proteinases to alter their destructive activity in arthritis, and as antiangiogenic factors to inhibit tumor spread.

Matrix metalloproteinase 3 (MMP-3) belongs to the stromelysin class of matrix metalloproteinases. MMP-3 is expressed in mature macrophages (Campbell et al. 1991), but also in endothelial cells, smooth muscle cells and fibroblasts. More recently, MMP-3 has been shown to be expressed in macrophage-derived foam cells from experimental atheroma (Galis et al. 1995). The inactive zymogen, proMMP-3, is activated by neutrophil elastase, plasma kallikrein, plasmin, chymotrypsin, trypsin, cathepsin G, and mast cell tryptase, as well as by mercurial compounds, such as 4-aminophenylmercuric acetate (APMA) (Nagase et al. 1992; Kleiner et al. 1993; Nagase et al. 1990; Nagase 1991). Elevated levels of MMP-3 have been found in the joints of patients suffering from osteoarthritis and rheumatoid arthritis. In atherosclerotic plaques there is a large amount of fibrin(ogen)-related antigen (FRA) consisting of different molecular forms (Bini et al. 1987; Bini et al. 1989; Smith et al. 1990; Valenzuela et al. 1992). Two very recent studies have shown the presence of matrix metalloproteinase 3 in atherosclerotic plaques (Henney et al. 1991; Galis et al. 1994), but its function in this context has remained unelucidated. Indeed, MMP-3 has been viewed in these studies as a potential negative factor.

The known substrates of MMP-3 include proteoglycans, collagen type IV, fibronectin, and laminin. Such substrates are typical of matrix metalloproteinases in general (Doolittle 1987). There has been no suggestion, however, that any endogenous metalloproteinase might be involved in the degradation of fibrinogen or fibrin. Nor has there been any indication that metalloproteinases could be used for fibrinolysis or thrombolysis.

From the foregoing discussion, it becomes clear that significant gaps exist in the understanding of processes involved in thrombus formation and degradation. While certain approaches have been identified which permit a measure of control over these processes, these approaches suffer serious deficiencies related to cost, efficacy, or safety. The diagnosis and treatment of disease states associated with physiological processes involving fibrinogen and fibrin have also been found lacking.

As a result, there exists a need for effective compositions and methods for use in limiting thrombus development and inducing thrombolysis.

There is a need for methods of disrupting blood clots and atherosclerotic plaques, both in vitro, such as for diagnostic purposes, and in vivo, such as for therapeutic treatment of embolism, atherosclerosis and other clinically important disorders.

In addition, there exists a need for diagnostic and experimental materials and methods for revealing more information concerning the physical and chemical processes involved in thrombus formation and degradation.

Moreover, there is a need for effective treatment to restore at least some integrity to a damaged vessel wall, to promote regression of atherosclerotic plaques, and to aid in angioplasty and bypass surgery to prevent reocclusion.

SUMMARY OF THE INVENTION

The present invention provides a method for degrading fibrin, fibrinogen, and related substances (i.e., "fibrin(ogen)") by means of a fibrinolytic metalloproteinase (FMP). Preferably, the fibrinolytic metalloproteinase is endogenous, more preferably, a stromelysin. Most preferably, the fibrinolytic metalloproteinase includes matrix metalloproteinase-3 (MMP-3). The fibrinolytic metalloproteinase preferably cleaves or degrades fibrin(ogen) at peptide bond designated γGly404-Ala405.

The inventive method can be performed in vitro. In vitro, the method involves contacting a tissue sample, such as blood or plasma, with at least one fibrinolytic matrix metalloproteinase. In this method, fibrin may be degraded as a constituent of clots and/or atherosclerotic plaques for purposes of investigating the structure of such materials, as well as for further investigation of the mechanisms of fibrinolysis and thrombolysis. Fibrinogen may be degraded for experimental or diagnostic purposes related to the formation of fibrin or to prevent potential growth of a fibrinogen-fibrin mesh.

In a preferred diagnostic method, the method includes contacting a sample containing fibrin(ogen) with at least one endogenous fibrinolytic metalloproteinase to provide degradation products. Preferably, the method includes analyzing the degradation products to characterize the fibrin(ogen).

Such analysis typically includes differentially separating the various degradation products. The degradation products can be identified or measured by various means. For example, the fragments can be detected through antibodies which specifically bind to or associate with particular region(s) of fibrin(ogen), or fail to associate with them due to loss of epitope induced by enzymatic degradation. Preferably, such antibodies are monospecific, more preferably monoclonal. Synthetic and/or chimeric antibodies may be used, as may antigen binding regions such as Fab and F(ab')$_2$. Measurement of specific association between such antibodies and degradation fragments can provide qualitative, or quantitative information about the fibrin(ogen) sample being analyzed. Such antibodies can be detectably labeled to aid in the measurement of the types and amounts of the degradation products. Alternatively, antibodies fixed to a substrate can be employed to aid in the separation or purification of degradation fragments produced by a fibrinolytic metalloproteinase.

The invention also provides a method of performing thrombolytic, embolytic, or atherolytic therapy in a vertebrate subject, preferably a primate, more preferably a human. In this embodiment, the invention involves administering to a subject a therapeutically effective amount of at least one endogenous fibrinolytic matrix metalloproteinase. Typically, the fibrinolytic metalloproteinase is administered in a therapeutic composition comprising the metalloproteinase and a pharmacologically acceptable carrier or diluent. Optionally, the administered composition can further include one or more other active ingredients as an adjunct to the fibrinolytic activity of the metalloproteinase. Suitable adjunct compounds include compounds having thrombolytic or fibrinolytic activity. For example, such adjunct compounds can be a plasminogen activator, hirudin, an enzyme inhibitor, an anticoagulant, an antibody or synthetic peptide specific for platelet gpIIb/IIIa receptor, or a combination thereof The method can be used prevent or ameliorate complications associated with atherosclerosis (i.e., to degrade fibrinogen and fibrin in plaques before occlusion occurs), as well as to prevent reocclusion following thrombolytic therapy, e.g., with t-PA, following myocardial infarction. In fact, t-PA is fast-acting, while a preferred metalloproteinase MMP-3 has a slower and progressive action. Thus, the compounds can be beneficially used in combination, including sequential or concurrent usage. The method can also be used as a prophylactic agent to inhibit restenosis following surgical intervention, such as bypass surgery or angioplasty. Alternatively, the method can be used in atherolytic therapy, to inhibit the initial formation, or promote the regression, of atherosclerotic plaques.

In addition, the invention provides diagnostic and therapeutic kits which include a fibrinolytic matrix metalloproteinase. The fibrinolytic metalloproteinase is preferably endogenous. Preferably, the metalloproteinase includes a stromelysin, more preferably MMP-3. It is also preferred that the metalloproteinase cleave or hydrolyze fibrin(ogen) at the γGly404-Ala405 peptide bond. Such kits can include one or more containers, as well as additional reagent(s) and/or active and/or inert ingredient(s) for performing any variations on the inventive method. Exemplary reagents include, without limitation, synthetic substrates to test enzymatic activity, and antibodies (preferably monospecific, e.g., monoclonal) to measure increase or decrease of antigen level. Preferred kits include at least one therapeutically effective unit dose of a fibrinolytic metalloproteinase. Also preferred are kits which include means for administering, preferably parenterally, more preferably intravenously, a composition containing a fibrinolytic metalloproteinase. The kits can include one or more other active ingredients as adjuncts, such as plasminogen activators, hirudin, or anticoagulants such as heparin or aspirin. These other ingredients can be included in separate compositions in separate reagent containers, or can be included with each other and/or the fibrinolytic metalloproteinase in a single reagent container. The kits can also include instructions for mixing or combining ingredients and or use of the kit according to the invention.

The invention further provides a method of controlling formation of thrombus caused by medical-related apparatus. In this embodiment, the method includes contacting a medical-related apparatus with a composition which includes a fibrinolytic matrix metalloproteinase, preferably MMP-3. The metalloproteinase desirably adheres or binds to a surface of the apparatus. The method can be used to modify blood-contacting surfaces of implantable prosthetic devices such as cannulae, catheters, grafts, stents, filters, coils, valves, and the like, to provide surfaces which inhibit the formation of clots or plaques. Alternatively, the method enables the fibrinolytic modification of apparatus such as needles, blood collection tubes, culture flasks, test plates, pipets, reagent containers, tubing, membranes, and the like, to promote fibrinolysis and to inhibit the polymerization of fibrinogen and the formation of thrombus which might otherwise interfere with the experimental protocols. Likewise, the invention provides medical-related apparatus such as implantables, labware, and other devices for in vivo and in vitro uses, which apparatus has been modified to include adhered fibrinolytic metalloproteinase.

In still another embodiment, the invention provides a method of enhancing the regulation of fibrinolysis in a subject in need of such therapy. In this embodiment, the method of the invention includes inducing enhanced regulation of an endogenous fibrinolytic matrix metalloproteinase in a subject. Preferably, the method involves increasing the activity or expression of an endogenous fibrinolytic matrix metalloproteinase by treating the subject with somatic cell gene transfer therapy. Alternatively, the method involves decreasing the activity or expression of an endogenous fibrinolytic matrix metalloproteinase by treating the subject with somatic cell gene transfer therapy. Other therapeutic approaches can be employed which involve pharmaceutical compositions for either promoting or inhibiting the activity or the expression of an endogenous fibrinolytic matrix metalloproteinase.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

Figure 1:
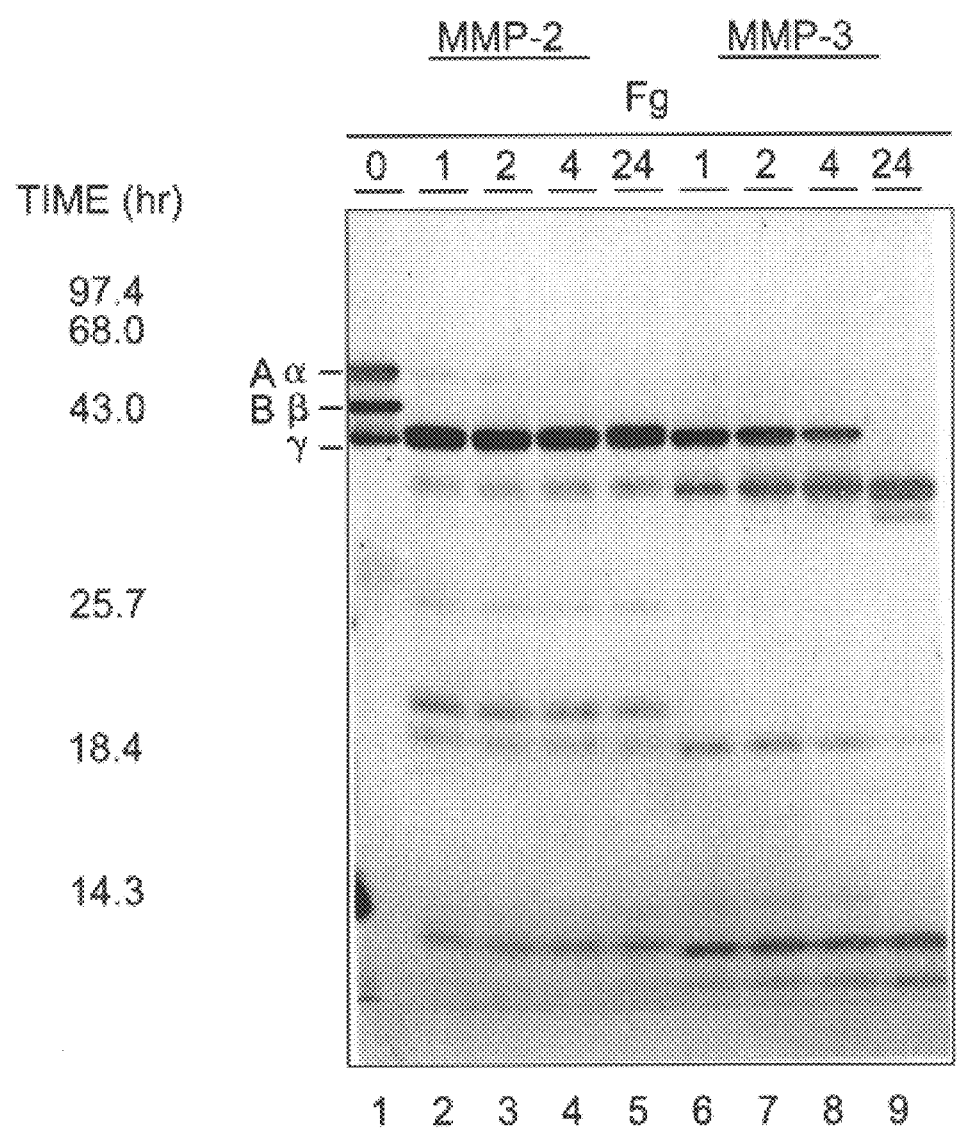
FIG. 1 shows an electrophoretic analysis of fibrinogen treated with MMP-2 or MMP-3, showing differential degradation of fibrinogen by each of the enzymes.

As noted above, two very recent studies have identified the presence of MMP-3 in atherosclerotic plaques (Henney et al. 1991; Galis et al. 1994). These studies have regarded the presence of MMPs in the plaques as a negative factor which might favor fissure of the plaques. The present invention, however, is consistent with an entirely different understanding of the function of MMP-3. The invention relates to the unexpected role which MMP-3 has been discovered to play in the degradation of fibrinogen and fibrin.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional, albeit not inconsistent, interpretations can be implied.

For example, the invention relates to the use of a matrix metalloproteinase to degrade fibrin and fibrinogen. The matrix metalloproteinases useful according to the invention must exhibit some enzymatic activity against fibrin, fibrinogen, and or related proteins, polypeptides, or oligopeptides. Matrix metalloproteinases which exhibit this activity are termed "fibrinolytic matrix metalloproteinases" or "fibrinolytic MMPs".

The fibrinolytic matrix metalloproteinase can be exogenous or endogenous. It is preferred that the fibrinolytic metalloproteinase be endogenous. As used herein, the term "endogenous" means that the fibrinolytic metalloproteinase have an origin in the species in which the method of the invention is to be performed. The species can be any vertebrate, preferably a mammal, and more preferably a primate. Most preferably, the method is performed in a human subject. Accordingly, when the method of the invention is employed in a human subject, it is preferred that the active metalloproteinase be endogenous to humans, i.e., of human origin, whether employed as a pharmaceutical composition or resulting from therapy designed to improve the subject's internal control of his/her fibrinolytic system. For in vitro procedures, the origin of the fibrinolytic metalloproteinase is less critical, but it is preferred that the metalloproteinase have an origin as close as possible to the species origin of the biological sample being examined. In such methods, the metalloproteinase is endogenous to the sample if it is derived from the species to which the tested sample belongs.

Preferred endogenous fibrinolytic metalloproteinases include any of the stromelysin class of metalloproteinases. Preferred stromelysins include MMP-3 (stromelysin-1), MMP-10 (stromelysin-2), and MMP-11 (stromelysin-3). A highly preferred endogenous fibrinolytic MMP is MMP-3. We have found that MMP-3 hydrolyzes fibrin(ogen) at the γGly404-Ala405 peptide bond in the cross-linking region of the gamma chain.

It is known that, due to the fluidity and complexity of the physiology of fibrin formation and degradation, many forms of fibrin and fibrinogen are present in the circulating blood as well as in thrombotic and atherosclerotic lesions. The many forms of these molecules result from continual assault by proteolytic enzymes which variously cleave the molecules. The method of the invention is performed by means of a fibrinolytic MMP which has activity against at least one fibrinogen- or fibrin-related compound. If a fibrinogen-derived molecule has previously been cleaved or modified to delete all MMP cleavage sites, then that molecule is no longer capable of acting as a substrate for a fibrinolytic MMP. Substrates for MMP-3 have now unexpectedly been found to include, inter alia, native fibrinogen and fibrin, and would also be expected to include modified, synthetic, and semisynthetic forms of these compounds, as well as a large number of cleavage products of these compounds. The class of substances which are derived from or related to fibrinogen and/or fibrin can be termed "fibrin(ogen)". The method of the invention can, therefore, be performed using any MMP which acts to degrade a fibrin(ogen) moiety. While such enzymes are generally termed "fibrinolytic", they can also be more precisely termed "fibrin(ogen)olytic" MMPs.

Fibrinogen (also abbreviated herein as "Fg") is known to be a homodimeric protein, in which each monomer includes three substantially homologous polypeptide chains, identified as the α (alpha), β (beta), and γ (gamma) chains. For a review see Doolittle (1987). Thus, fibrinogen has the structure $(\alpha\beta\gamma)_2$. All three fibrinogen subunits have coiled domains which permit the subunits to engage one another to form a "coiled coil" region in the fibrinogen monomer. In addition, the beta and gamma chains each have a globular domain, while the alpha chain is present in two forms; a predominant form having no corresponding globular domain (α), and a less prevalent form in which a globular domain is present ($\alpha_E$) (Fu et al. 1994). Accordingly, because fibrinogen is homodimeric and because two forms of the alpha subunit have been identified, two principal forms of fibrinogen are known: $(\alpha\beta\gamma)_2$ and $(\alpha_E\beta\gamma)_2$. Both forms of fibrinogen are considered to be substrates of fibrinolytic MMPs according to the invention. Artificial heterodimers of fibrinogen, as well as recombinant forms are also within the class of fibrinolytic MMP substrates.

As noted, fibrin (also abbreviated herein as "Fb") is generated through an induced and controlled polymerization of fibrinogen (Fu et al. 1994). Given that various forms of fibrinogen are known in circulating blood, it is known that various polymerization structures for fibrin occur. Fibrin structure can affect the processes of fibrinolysis (Gabriel et al. 1992). A fibrinolytic metalloproteinase has now been found to effectively lyse fibrin. It appears, therefore, that fibrinolytic metalloproteinases are active against fibrin without being substantially limited by peculiarities of fibrin cross-linking. Accordingly, fibrin is considered to be an MMP substrate according to the invention. Thus, fibrin which occurs naturally in a subject is suitable for degradation according to the invention, as is fibrin induced in vitro. Thus, clots which are induced in blood ex vivo, e.g., in a blood sample, can be degraded according to the invention. In such in vitro applications, a fibrinolytic metalloproteinase can be employed as a coating on a container such as blood collection tube. Also, artificial fibrin, formed from natural, synthetic, semisynthetic, recombinant and/or other types of fibrinogen can also be degraded by the method described herein.

Under physiologic conditions, plasmin is the central enzyme which acts to degrade fibrin. Plasmin action is restricted to the site of fibrin deposition by plasma control mechanisms that prevent proteolysis of circulating proteins. However, under pathologic conditions, plasmin is known to degrade plasma proteins, especially fibrinogen.

Degraded fibrinogen can be separated by ion-exchange chromatography into five fractions (A, B, C, D, and E), of which fragments D and E are the major end products of the original molecule. The identification and characterization of the transient intermediate fragments X and Y engendered the insight for the development of an asymmetric scheme of fibrinogen degradation Francis et al. 1994).

Classically, fibrinogen structure is bilaterally symmetrical, including a central globular domain E which is a "knot" made up of the N-terminal regions of all six chains in the fibrinogen molecule. From E extend two coiled coils each of which contains portions of one set of $\alpha$, $\beta$, and $\gamma$ chains. At the other ends of the coiled coils are globular domains D. Extending from the D domains, are the A$\alpha$ chain extensions, which, in the $\alpha_E$ subunit only, terminate in another globular domain.

Under proteolytic attack by plasmin, initial cleavages liberate the carboxy-terminal, polar appendage of the A$\alpha$ chain, and a peptide from the N-terminal portion of the B$\beta$ chain (B$\beta$1-42). The remaining major fragment is Fragment X. Cleavages of all three polypeptide chains along one coiled coil connecting the central N-terminal knot (E) and a terminal (D) domain of fragment X split it asymmetrically. The result is one fragment D molecule, which consists of carboxy-terminal portions of the three chains, and a fragment Y moiety, consisting of central and terminal domains still connected by a coiled coil. Subsequent cleavage of the coiled coil of fragment Y produces a second fragment D and a fragment E moiety. Fragment X is slowly coagulable by thrombin, but fragments Y and D have potent antipolymerizing effects, due mostly to disruption of the proper alignment and continuation of build-up of the protofibrils of fibrin.

Knowledge of the conventional fragmentation of fibrinogen assists in providing a conceptual framework against which to compare the activity of other potential fibrinolytic enzymes. Moreover, antibodies have been developed which are specifically reactive with or specifically bind to only some of the fragments, thereby permitting molecular identification of fragments with great accuracy and precision (Kudryk et al. 1989a). Using this knowledge, fibrinolytic activity of an endogenous metalloproteinase has now been unexpectedly identified, thereby enabling the development of the method of the invention.

The invention provides, inter alia, a method of degrading fibrin(ogen). Generally, the method requires the use of an endogenous matrix metalloproteinase which possesses enzymatic activity against, i.e., can hydrolyze, fibrin and/or fibrinogen. The method includes contacting fibrin or fibrinogen with an effective amount of a fibrinolytic matrix metalloproteinase, preferably MMP-3.

The method typically involves contacting fibrinogen or fibrin with a matrix metalloproteinase. Compositions including a fibrinolytic metalloproteinase can also include other active and/or inert ingredients. Other active ingredients can include such ingredients as inhibitors of MMPs, plasminogen activators, other fibrinolytic enzymes, anti-coagulation reagents, etc. Should another active ingredient be employed, it is preferred to include in the composition a plasminogen activator. It has been found that matrix metalloproteinase 3, in particular, does not compete substantially with or substantially inhibit t-PA or plasmin. Accordingly, the method of the invention can include plasminogen activators such as u-PA, t-PA, staphylokinase, streptokinase or recombinant, synthetic, or semisynthetic forms thereof The invention also now permits the investigation of the interaction of MMP-3 with plasminogen activators, plasminogen activator inhibitors (e.g., PAI-1), and native plasminogen. For example, while it is known that plasmin can activate MMP-3, it is not known whether MMP-3 activates t-PA or u-PA, or if it might be activated by them instead. Nor is it known if MMP-3 might activate native plasminogen.

It may also be desirable to include an anticoagulation agent such as heparin, to inhibit or prevent re-coagulation. Such measures would be less critical in in vitro applications, but could be significantly helpful in in vivo applications. The combination of t-PA with heparin to define a dual-functional thrombolytic composition is illustrated in U.S. Pat. No. 5,130,143.

In one preferred embodiment, the method of the invention permits fibrinolytic therapy of a mammalian, preferably human, subject. In this embodiment, the method includes the administration to a subject of a therapeutically effective amount of a matrix metalloproteinase which degrades fibrin (ogen). The metalloproteinase preferably includes an endogenous metalloproteinase, more preferably a stromelysin, and most preferably MMP-3. The therapeutic method can be employed for thrombolysis, or for prevention of progression and facilitation of regression of atherosclerotic plaques. Thus, the method can be performed for acute or emergency therapy or for prolonged or chronic maintenance therapy to reduce the likelihood of or inhibit the development of abnormal thrombi, emboli or atherosclerotic plaques.

Modes of administration of such a composition are known in the art, and are related to those techniques employed in the administration of conventional thrombolytic agents. Such methods include, without limitation, parenteral methods, preferably intravascular methods such as intravenous injection, intraarterial injection, and administration by catheter.

The determination of the effective amount of a composition of the invention is within the discretion of the skilled clinician. Specific prophylactic or therapeutic dosages and the timing of administration can be selected depending upon prevailing conditions to achieve clinically acceptable treatment. The skilled clinician will take into account such factors as the age, sex, weight, and condition of the subject, as well as the route of administration. The skilled clinician will also recognize that the fibrinolytic activity of MMPs can be enhanced by the collateral administration (e.g., co-administration or sequential administration) of other active and/or inert substances. For example, it can be desirable to administer adjunct agents having thrombolytic activity. These agents can have direct fibrinolytic activity or can be regulators or modulators of fibrinolysis in the system in which they are employed. For example, agents having thrombolytic activity include plasminogen activators, hirudin, enzymes (e.g., proteases derived from snake venom), enzyme inhibitors, anticoagulants (e.g., heparin, aspirin), antibodies (preferably monoclonal antibodies) or synthetic peptides specific for platelet gpIIb/IIIa receptor, or a combination thereof. Various such thrombolytic agents are described in Collen (1996). These agents can be administered together with or ancillary to the administration of an MMP-containing composition. Thus, such other agent or agents can be included in the metalloproteinase-containing composition, or can be administered as part of another composition.

In another embodiment, the invention includes targeted fibrinolytic metalloproteinases, i.e., metalloproteinases which are bound to moieties having specificity for a biological target molecule. For example, a metalloproteinase can be bound to an antibody by methods known in the art for attaching proteins to antibodies. In this way a metalloproteinase can be preferentially directed to a fibrin(ogen) substrate for improving fibrin(ogen)olytic efficacy. Thus, a fibrinolytic metalloproteinase such as MMP-3 can be linked to antibodies having specificity for fibrin or a degradation product thereof, to platelets, specifically to P-selectin, to oxidized lipoproteins, etc.

The invention also provides a diagnostic method for the characterization of fibrinogen. In this method, fibrin(ogen) is contacted with an endogenous matrix metalloproteinase, preferably MMP-3, to produce degradation products. The degradation products are then analyzed to determine the types and amounts of cleavage products generated by the activity of the MMP.

Typically, the method involves the differential separation of degradation products, such as separation of the products by gel electrophoresis. The products are then measured such as by non-specific staining to reveal quantities of products of different sizes. Alternatively, the products can be identified by contacting the products with antibodies which are specifically reactive with or specifically associate with one or more domains of fibrin(ogen) (Kudryk et al. 1989a). Preferably, such antibodies are specifically reactive with a single degradation product, thereby permitting characterization of the product in relation to other products.

New antibodies, useful according to the diagnostic method of the invention, can be developed and detectably labeled with any detectable marker group. Suitable marker groups include, for example, fluorescent labels, enzyme labels, and radioactive labels. Detector groups useful according to the invention include, for example, fluorescein as a fluorescent label, horseradish peroxidase as an enzyme label, and Iodine-125 ($^{125}$I) as a radioactive label. Additional fluorescent labels which can be utilized in the invention include, but are not limited to, rhodamine, phycoerythrin and additional compounds emitting fluorescent energy. Additional enzyme labels which can be utilized in this invention include, but are not limited to, glucose oxidase and alkaline phosphatase. Additional radioactive labels which can be utilized in this invention include, but are not limited to, Iodine-131 ($^{131}$I) and Indium-111 ($^{111}$In).

Suitable detectable labels can be selected from among those known in the art, such as radioactive labels, enzymes, specific binding pair components, colloidal dye substances, fluorochromes, reducing substances, latexes, digoxigenin, metals, particulates, dansyl lysine, antibodies, protein A, protein G, electron dense materials, chromophores, and the like. Effectively, any suitable label, whether directly or indirectly detectable, can be employed. One skilled in the art will clearly recognize that these labels set forth above are merely illustrative of the different labels that could be utilized in the diagnostic method of the invention.

Fibrinogen subunit-reactive antibodies can also be derivatized by conjugation to biotin, and used, upon addition of species of avidins which have been rendered detectable by conjugation to fluorescent labels, enzyme labels, radioactive labels, electron dense labels, etc., in a multiplicity of immunochemical and immunohistological applications.

Alternatively, the method of the invention can be performed using antibodies which have been attached or bound to substrates materials according to methods known to those skilled in the art. Such materials are generally substantially solid and relatively insoluble, imparting stability to physical and chemical disruption of the antibodies, and permitting the antibodies to be arranged in specific spatial distributions. Among substrate materials, materials can be chosen according to the artisan's desired ends, and include materials such as gels, hydrogels, resins, beads, nitrocellulose, nylon filters, microtiter plates, culture flasks, polymeric materials, and the like, without limitation.

The method of the present invention can involve immunological assays to determine the presence of fibrin(ogen) breakdown products in tissue samples from human or animal subjects. Biopsy and necropsy samples of subjects, as well as samples from tissue libraries or blood banks, can be evaluated for the presence of fibrin(ogen) MMP breakdown fragments using an anti-fibrinogen antibodies. Moreover, suitable preparations can be devised for in vivo use, such as for the visualization of fibrinogen or fibrinogen-containing substances and structures in a living subject. In this way the progression of fibrinolysis induced by MMPs can be assessed in situ.

In one such embodiment, an endogenous fibrinolytic MMP, preferably MMP-3, is bound to a substrate material such as a membrane, blood collection tube, microtiter plate, culture flask, or the like. In this manner, the method of the invention can be performed in the absence of soluble MMP, to induce fibrin(ogen)olysis in a fluid sample. Alternatively, this approach is useful in coating membranes and prosthetic devices.

Indeed, in another embodiment, the invention provides a method of controlling formation of clots or plaques caused or induced by medical-related apparatus. In this embodiment, the method includes contacting a medical-related apparatus with a composition which includes a fibrinolytic matrix metalloproteinase, preferably MMP-3. This method can be used to cause a metalloproteinase to bind or adhere to a surface. It is believed that any apparatus which would contact blood can be so modified by methods known in the art which permit the attachment of proteins to substrate materials. For example, the method can be used to modify blood-contacting surfaces of implantable prosthetic devices such as cannulae, catheters, grafts, stents, filters, coils, valves, and the like, to provide surfaces which inhibit the formation of thrombus. Alternatively, the method enables the fibrinolytic modification of apparatus such as blood collection tubes, culture flasks, test plates, pipets, reagent containers, tubing, membranes, and the like, to promote fibrinolysis and to inhibit the formation of thrombus which might otherwise interfere with the experimental protocols. Likewise, the invention provides medical-related apparatus such as implantables, labware, and other devices for in vivo and in vitro uses which possess the capacity or inhibiting thrombus formation by promoting the degradation of fibrin(ogen). The metalloproteinase can be adhered to an apparatus either permanently or reversibly, such as for delivery of metalloproteinase from an apparatus into solution.

The invention also provides a method of enhancing regulation of fibrinolysis in a subject in need of such therapy. In this embodiment, the method of the invention includes inducing enhanced regulation of an endogenous fibrinolytic matrix metalloproteinase in a subject. Preferably, the method involves increasing or decreasing the activity or expression of an endogenous fibrinolytic matrix metalloproteinase by treating the subject with somatic cell gene transfer therapy. Any gene therapy approach can be employed according to this embodiment. Thus, up-regulation of MMP expression can be accomplished by introducing a gene for a fibrinolytic MMP by ex vivo or in vivo gene transfer techniques. Alternatively, up-regulation of an MMP can be accomplished by inhibiting the expression of an MMP inhibitor via anti-sense technology. Down-regulation of MMP activity can be accomplished by these techniques, the design and implementation of which are within the skill of those in the art. A brief overview of several gene therapy methods is provided in Glick et al. (1994), which is incorporated herein by reference. Other therapeutic approaches can be employed which involve pharmaceutical compositions for either promoting or inhibiting the activity or the expression of an endogenous fibrinolytic matrix metalloproteinase. Given the complexity of the fibrinolytic regulation system, and given the unexpected role of MMPs in that regulatory scheme, it would appear to those skilled in the art that many potential avenues exist for adjustment of the fibrinolytic regulatory status of a subject.

The following examples are intended to assist in a further understanding of the invention. The particular materials and conditions employed are intended to be further illustrative of the invention and are not limiting upon the reasonable scope thereof In the following examples, we describe our experiments which have revealed the role that MMPs, particularly MMP-3, play in the degradation of fibrinogen (Fg) and cross-linked fibrin (XL-Fb). We have studied the following aspects: 1) degradation of Fg; 2) effect of MMPs-digestion of Fg on its subsequent clottability with thrombin; 3) lysis of XL-Fb and purified Fragment D-dimer (DD); 4) $NH_2$-terminal analyses of chain fragments of selected digests; 5) reactivity of the cleaved fragments with a number of specific monoclonal antibodies. We show the ability of MMP-3 to degrade Fg and to lyse XL-Fb clots. Based on this work, we conclude that both matrix metalloproteinase 1 (MMP-1) and matrix metalloproteinase 2 (MMP-2 ) can partially degrade Fg, and that MMP-2 has a limited capacity to degrade XL-Fb. We have also determined that, in XL-Fb, the γGly404-Ala405 bond is a major MMP-3 cleavage site, leading to the formation of a Fragment D-like monomer. This indicates a specific mechanism of fibrin degradation, different from plasmin, by an endogenous enzyme.

The following experimental procedures are relevant to Examples 1–9, below:

Proteins and Other Reagents. Plasminogen-free and fibronectin-free Fg (Fg≧95% clottable) or lyophilized human Fg were purchased (American Diagnostica Inc., Greenwich, Conn.). Plasminogen and fibronectin were removed by affinity chromatography on lysine-Sepharose and gelatin-Sepharose, essentially as described by others (Deutsch et. al. 1970; Engvall et al. 1977; Procyk et al. 1985). The amount of Factor XIII in these preparations is 0.1–0.2 Loewy units/mg of Fg according to the manufacturer. Stock solutions of Fg (12 mg/mL in TNE buffer (0.05M Tris-HCl (pH 7.4), containing 0.1M NaCl, 0.001M EDTA and 100 KIU/mL aprotinin)) were stored at −70° C. until used. Fg concentration was measured spectrophotometrically in alkaline-urea using extinction coefficient (1%, 1 cm)=16.5 at 282 nm. Human Glu-Plasminogen (1 U/0.5 mg) was from Imco (Stockholm, Sweden). Streptokinase (4500 u/mg solid), bovine serum albumin (BSA, Fraction V, RIA-grade), 4-aminophenylmercuric acetate (APMA) and EDTA were from Sigma Chemical Company (St. Louis, Mo.). Aprotinin was from Mobay Chemical Corp (New York, N.Y.). Human α-thrombin (2300 U/mg) was a generous gift of Dr. J. Fenton. $^{125}$I-Fg, labeled by the iodogen method (specific activity $1.5 \times 10^6$ cpm/μg protein) was a generous gift of Drs. M. Nag and D. Banerjee, Laboratory of Membrane Biochemistry II, The New York Blood Center. Pro-MMP-1, pro-MMP-2, and pro-MMP-3 were purified as previously described by others (Okada et al. 1986; Okada et al. 1990; Suzuki et al. 1990). All other reagents were of analytical grade and were purchased from Fisher Scientific (Springfield, N.J.).

Gel electrophoresis/Immunoblotting. Samples of Fg and XL-Fb degraded with plasmin or MMPs were subjected to SDS-PAGE using both reducing and non-reducing conditions. Reduced samples were prepared in 62.5 mM Tris buffer, pH 6.8, containing 4% SDS, 8M urea, 5% DTT, 10% glycerol and 1% bromphenol blue. Non-reduced samples were made in the same buffer without DTT. SDS-PAGE was performed using 5–15% gradient or 12.5% polyacrylamide gels in Tris-glycine buffer (Laemmli 1970) or with 5% and 7.5% mini gels in phosphate buffer (McDonagh et al. 1972) following general procedures. Prestained molecular weight standards used were myosin (200 kDa), phosphorylase B (97.4 kDa), BSA (68 kDa), ovalbumin (43 kDa), α-chymotrypsinogen (25.7 kDa), β-lactoglobulin (18.4 kDa) and lysozyme (14.3 kDa) (Bethesda Research Laboratories, Gaithersburg, Md.). Transfer to nitrocellulose membranes for immunoblot analyses was performed as described by Towbin et al. (1979) with few modifications (Kudryk et al. 1989b). In some experiments, membranes were stained with colloidal gold prior to immunoblotting (Colloidal Gold Total Protein Stain, BioRad, Hercules, Calif.). Membranes were blocked with 5% dry milk (Carnation, Nestle, Glendale, Calif.) or with 5% BSA, incubated overnight with a selected primary antibody (Table I) and then probed with a second antibody. Rabbit anti-mouse-horseradish peroxidase (RAM-HRPO) was prepared as described by Goding (1986) using RAM purchased from Dako (Carpinteria, Calif.) and HRPO (type VI) from Sigma. Bound peroxidase complexes were detected using the chemiluminescent substrate Luminol (ECL Western blotting detection system, Amersham Life Science, Arlington Heights, Ill.). Light emitted from the hydrolysis of the added Luminol substrate exposed the provided film (Kodak χ-Omat RP, Eastman Kodak Company, Rochester, N.Y.) in 10 to 30 seconds.

EXAMPLE 1

Degradation of Fibrinogen. An experiment was performed to evaluate whether MMPs possess fibrin(ogen)olytic activity. Fibrinogen (Fg) (120 μg, 3.5 μM) was incubated with MMP-2 or MMP-3 (6 μg/ml or 1:20 E:S ratio) at 37° C. for different time intervals. ProMMP-2 and pro-MMP-3 (in 50 mM Tris-HCl, pH 7.5, 0.15M NaCl, 0.05% Brij 35, 0.05% NaN$_3$) were activated with 1 mM APMA at 37° C. for 45 min and 24 hr, respectively, prior to addition to the Fg solutions. All reactions were in the presence of 10 mM CaCl$_2$ at 37° C. Digestions were terminated by addition of EDTA (25 mM final concentration). Reaction products were mixed with reducing or non-reducing buffer and subjected to SDS-PAGE separation (12.5%). The gels were stained for protein with Coomassie blue.

FIG. 1 shows the time-dependent digestion of fibrinogen by MMP-2 and MMP-3 by comparison to non-digested fibrinogen. The enzymes were used at E:S=1:20 (w/w) and incubation was for 1, 2, 4 and 24 hrs. The key to FIG. 1 is as follows:

| Lane No. | Sample |
| --- | --- |
| 1 | Non-digested fibrinogen |
| 2 | MMP-2 digest of Fg (1 hr) |
| 3 | MMP-2 digest of Fg (2 hrs) |
| 4 | MMP-2 digest of Fg (4 hrs) |
| 5 | MMP-2 digest of Fg (24 hrs) |
| 6 | MMP-3 digest of Fg (1 hr) |
| 7 | MMP-3 digest of Fg (2 hrs) |
| 8 | MMP-3 digest of Fg (4 hrs) |
| 9 | MMP-3 digest of Fg (24 hrs) |

It is clear from FIG. 1 that, using MMP-2 and MMP-3 in comparable amounts (6 μg/120 μg Fg), both the Aα- and Bβ-chains of Fg were extensively degraded in 1 hr (lanes 2 and 6). A longer (24 hr) incubation resulted in further cleavage of both chains (lanes 5 and 9). Degradation of Fg γ-chains with MMP-3 was extensive at 24 hr (FIG. 8, lane 9) and different from that with MMP-2 (lane 5). Significant degradation with MMP-2 and MMP-3 was also obtained at lower concentration of enzyme (0.2–0.6 μg/120 μg Fg, data not shown). MMP-1, was also tested using this protocol, and, at the highest concentration (6 μg/120 μg Fg), showed apparently intact Bβ- and γ-chains and only partial degradation of the Aα-chains (data not shown).

EXAMPLE 2

Coagulability of Fibrinogen Degraded with MMP-3. Digests (1.5 and 3 hrs) of fibrinogen with MMP-2 and MMP-3 were prepared as described above. A plasmin digest of Fg (18–20 hr) (Gårdlund et al. 1972) was used as control. Intact Fg and Fg digests were clotted with thrombin as described by Bini et al. (1994). Briefly, 1.2 mg Fg/mL, or any of the above MMP-2 and MMP-3 digests of fibrinogen, was clotted with thrombin (0.4 NIH U/mL) in the presence of 20 mM CaCl$_2$. Clotting time was determined as an increase in turbidity and read at 350 nm (Blombäck et al. 1982). Coagulability was determined from the plot of turbidity versus time. A tangent was drawn to the steepest part of the curve; its intersection with the time axis is defined as clotting time (Blombäck et al. 1994). In all cases, the gels were formed without any observed precipitation. Clot supernatants were run on HPLC (Kudryk et al. 1989b) in order to determine release of fibrinopeptides A (FPA) and B (FPB). These results are tabulated in Table I, below.

TABLE I

| Sample | E:S w/w | Incubation Time (hrs) | Thrombin Time | Turbidity (same day) | Turbidity (next day) |
| --- | --- | --- | --- | --- | --- |
| Fg control[a] Enzymes: | — | — | 68" | 0.841 | 0.973[b] |
| MMP-2 | 1:200 | 1.5 | >10 min | 0.433 | 0.963 |
|  |  | " | " | 0.377 | 0.823 |
|  |  | 3 | >10 min | 0.681 | 1.039 |
|  |  | " | " | 0.758 | 1.125 |
| MMP-3 | 1:600 | 1.5 | >10 min[c] | — | 0.025 |
|  |  | " | " | — | 0.035 |
|  |  | 3 | " | — | 0.004 |
|  |  | " | " | — | 0.029 |
| " | 1:200 | 1.5 | >10 min[d] | — | 0.001 |
|  |  | " | " | — | 0.000 |
|  |  | 3 | " | — | 0.008 |
|  |  | " | " | — | 0.012 |
| Plasmin | 1:1200 | 1.5 | 107.5" | 0.396 | — |
|  |  | " | 103.9" | 0.399 | — |
|  |  | 3 | 139.1" | 0.502 | — |
|  |  | " |  |  |  |
| " | 1:240 | 1.5 | unclottable | — | — |
|  |  | " | " | — | — |
|  |  | 3 | " | — | — |

[a]Fibrinogen (Fg) concentration in all samples: 120 μg/ml
[b]n = 5
[c]soft clot the next day at both 1.5 and 3 hrs
[d]no clot the next day Fg digested with MMP-2 (1.5 and 3 hr) did not clot within 10 min (arbitrarily taken as maximum time), but was still capable of forming a fibrin gel after overnight incubation with thrombin as shown by the turbidity data (Table I). By contrast, both MMP-3- and plasmim-digests, at comparable time and concentration, were unclottable even after overnight incubation. Turbidity data indicated that gelation was obtained only from reaction mixtures of Fg digested with MMP-2 and with the lowest plasmin concentration. Furthermore, turbidity values of the same preparations measured the next day showed that reaction mixtures of Fg and MMP-2 were similar to control while Fg digests generated by MMP-3 or plasmin had low or no turbidity (Table I). HPLC profiles of supernatants from all digests showed normal release of fibrinopeptides A and B with thrombin (not shown).

EXAMPLE 3

Degradation of Cross-Linked Fibrin. Fibrin clots were made from purified fibrinogen according to the method of Bini et al. (1994) and the references cited therein. Radiolabeled clots were made with 0.1 mL purified Fg (1.2 mg/mL in TNE buffer) containing $^{125}$I-Fg (20,000 cpm) in the presence of 20 mM CaCl$_2$. Thrombin (1.5 NIH U/mL, final concentration) was added and samples were incubated at 37° C. for 18–20 hrs (Bini et al. 1994). Active MMP-1, MMP-2, or MMP-3 were added in different amounts (2–60 μg/mL, corresponding to 1:600–1:20 E:S ratio) in the presence of 10 mM CaCl$_2$. Plasmin was generated by adding plasminogen (50 μg/mL) and streptokinase (1080 U/mL) to the fibrin clots (approximately 0.02–0.5 U/mL plasmin, final concentration, corresponding to 1:1200–1:48 E:S). Clots were gently dislodged from the wall of the test tube with a wooden stick and the content lightly vortexed after addition of each enzyme. Incubation times were from 1–48 hrs at 37° C. Digests with MMPs were terminated by addition of EDTA (25 mM final concentration), and those with plasmin were terminated with 5,000 KIU/mL aprotinin. Clots were separated from supernatants by centrifuging at 13,000 rpm for 20 min in a Sorvall RCL-B (SS-34 rotor). Fibrinolysis was measured both by release of radioactivity into the supernatant (A) and by residual radioactivity in each clot (B). Samples were counted in a Packard Auto-γ-5000 Series Gamma Counter. Control fibrin clots, with and without digestion with the different enzymes, were made at the same time to be used for SDS-PAGE. Data represent mean values of 2–4 separate experiments.

Figure 2A:
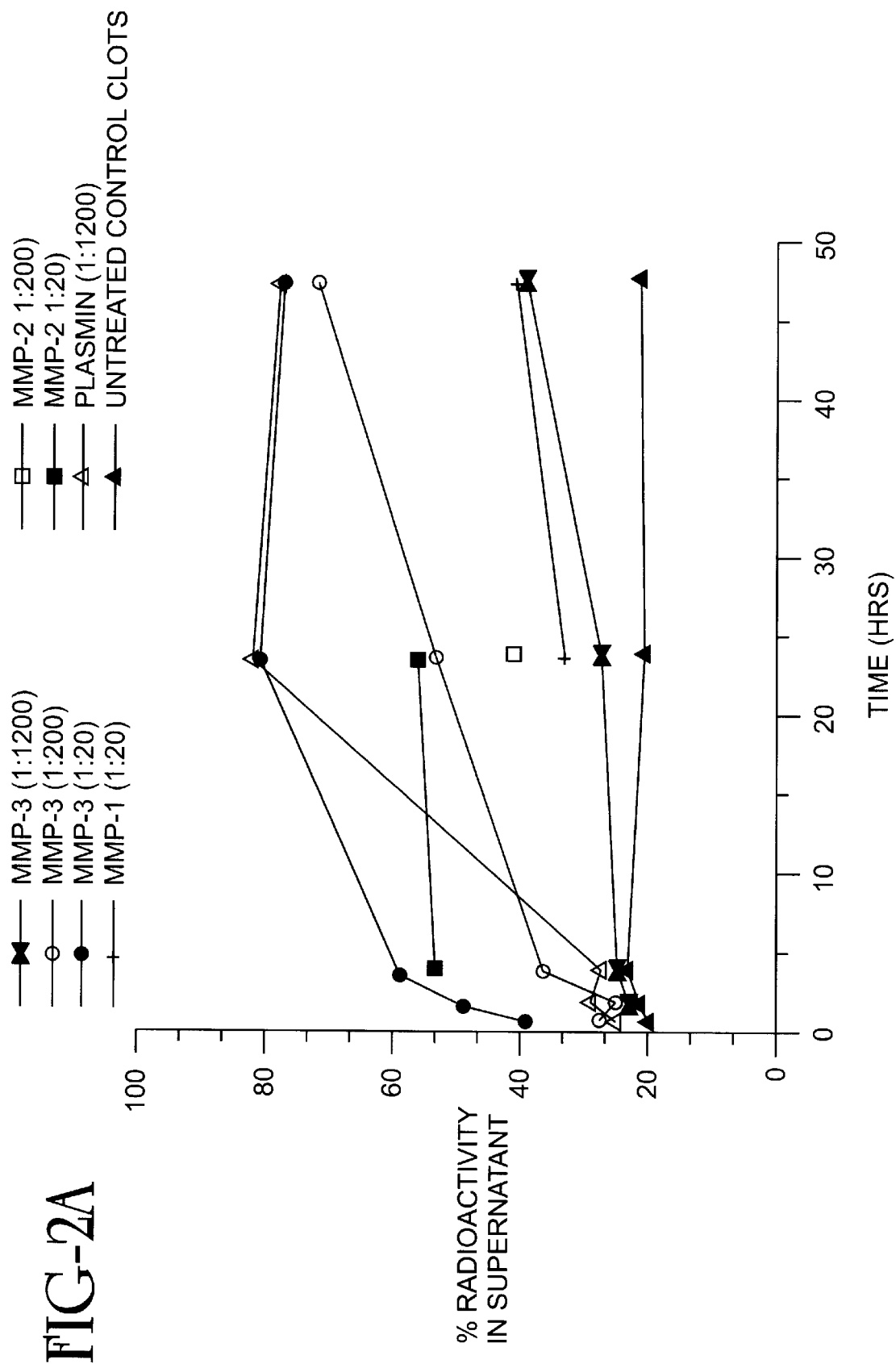
FIG. 2A is a graph illustrating comparative fibrin clot lysis by MMPs and plasmin as measured by the percentage of radioactivity in the sample supernatants.
Figure 2B:
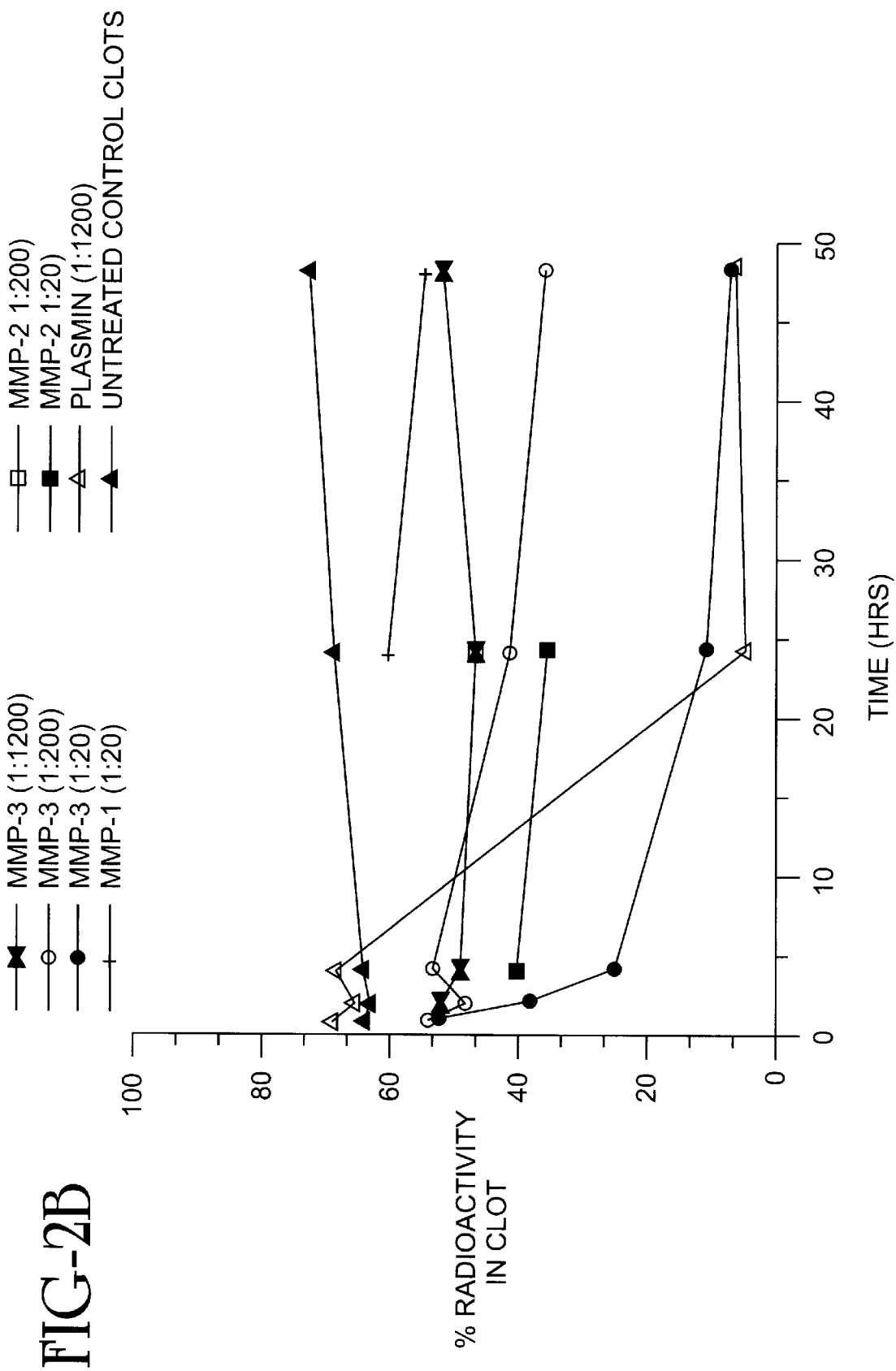
FIG. 2B is a graph illustrating comparative fibrin clot lysis by MMPs and plasmin as measured by the percentage of radioactivity in the residual clots.

The results of this experiment are presented in FIGS. 2A and 2B, which show the percent radioactivity in the supernatants (FIG. 2A) and in the residual clots (FIG. 2B). As shown, after 24 hours of incubation, both the MMP-3 (6 μg/120 μg Fg) and plasmin (0.02 IU/mL) samples showed release of over 80% of the radioactivity into the supernatants (average of three experiments) (FIG. 2A). Residual radioactivity in the clots at 24 hrs was less than 10% (FIG. 2B), and the clots appeared dissolved by both MMP-3 and plasmin. See FIGS. 2A and 2B. The concentration of plasmin used in the lysis experiments was chosen on the basis of obtaining a slow lysis (Liu et al. 1986). In preliminary experiments, similar release of radioactivity was measured in the supernatants using plasmin at 1:240 and 1:1200 (E:S, w/w), which was used throughout the study. Degradation with MMP-2 at highest concentration at 24 hr, was similar to that obtained with MMP-3 at 1:200. Degradation with MMP-1 at highest concentration, after 48 hr, was similar to MMP-3 at 1:1200. Controls, with no addition of enzyme as well as a plasmin digest of XL-Fb, are also shown.

Incubation with a mixture of MMP-3 and plasmin in the sample produced results similar to those produced by either enzyme alone (data not shown). This indicates that the two enzymes do not interfere with one another. Identical experiments were performed using clots made from plasma, and similar results were obtained (data not shown).

EXAMPLE 4

Chain Composition of XL-Fb Degraded by MMPs and Plasmin. The digestion of cross-linked fibrin by plasmin, MMP-2 and MMP-3 was analyzed. Samples of fibrin degradation by each of the enzymes were reduced and subjected to SDS-PAGE (5–15% gradient) (Laemmli et al. 1973; McDonagh et al. 1972). Following electrophoresis, resolved proteins were transferred to nitrocellulose. Protein was stained with colloidal gold on the nitrocellulose membrane. The patterns of dose-dependent and time-dependent degradation of fibrinogen and fibrin by MMP-2, MMP-3 and plasmin are shown in FIG. 3.

Figure 3:
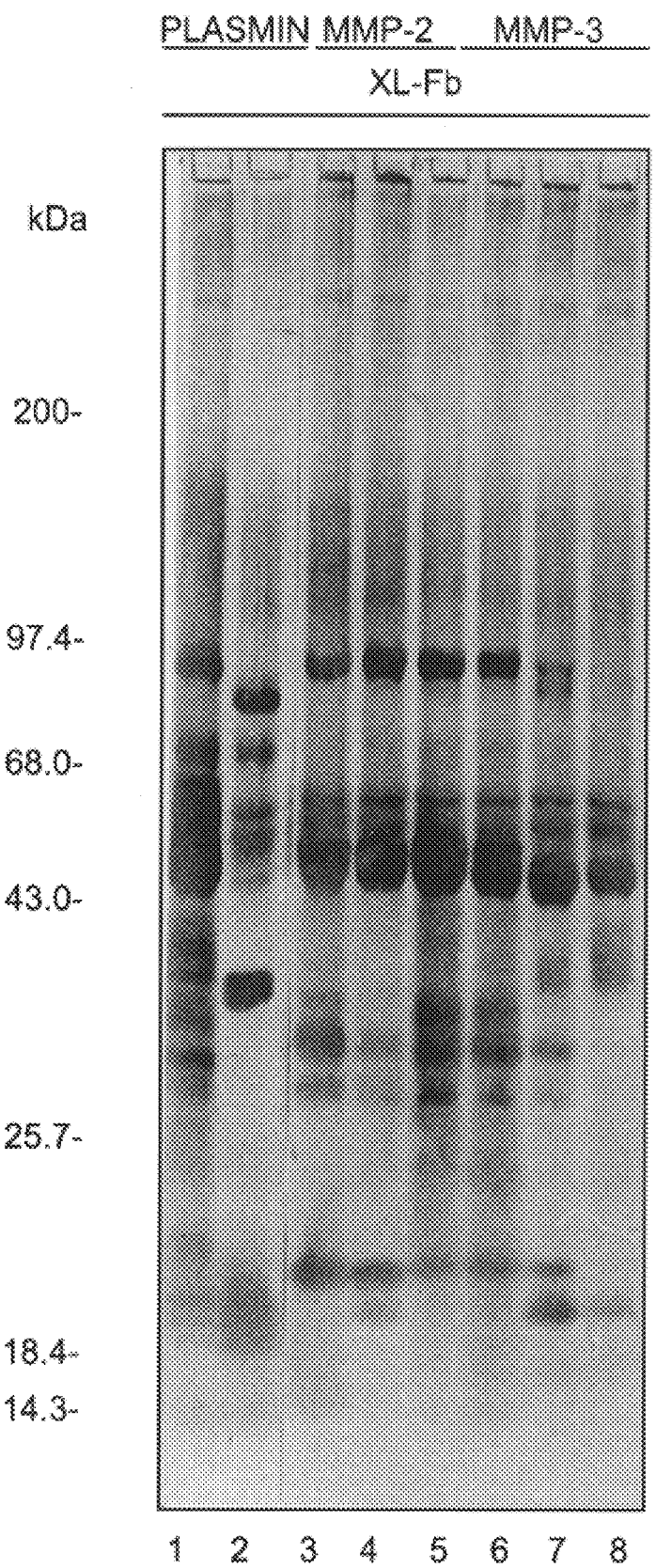
FIG. 3 shows an electrophoretic analysis of fibrin treated with MMP-2, MMP-3, and plasmin, showing differential degradation of fibrinogen by each of the enzymes.

The key to FIG. 3 is as follows:

| Lane No. | Sample |
|---|---|
| 1 | Fibrin degraded with plasmin (1:1200) for 24 hrs |
| 2 | Fibrin degraded with plasmin (1:240) for 24 hrs |
| 3 | Fibrin degraded with MMP-2 (1:200) for 24 hrs |
| 4 | Fibrin degraded with MMP-2 (1:20) for 24 hrs |
| 5 | Fibrin degraded with MMP-3 (1:600) for 24 hrs |
| 6 | Fibrin degraded with MMP-3 (1:200) for 24 hrs |
| 7 | Fibrin degraded with MMP-3 (1:20) for 24 hrs |
| 8 | Fibrin degraded with MMP-3 (1:10) for 24 hrs |

FIG. 3 shows plasmin degradation of cross-linked fibrin γ-dimer chain (94 kDa) into DD γ-dimer chain (76 kDa) at higher E:S ratio (lanes 1 and 2). No degradation of cross-linked fibrin γ-dimer was observed with MMP-2, at highest E:S (1:20) (lane 4). Significant degradation of the γ chain was obtained with MMP-3 (E:S=1:20) at 24 hrs (lane 7) and complete degradation was obtained by increasing E:S twofold (lane 8). The pattern of degradation of cross-linked fibrin γ-dimer chain by MMP-3 is different from that obtained with plasmin. In fact, plasmin decreases the molecular weight of the γ dimer, but does not monomerize it (lanes 1, 2) even at higher E:S ratio (1:240).

The XL-Fb clots were gradually degraded by MMP-3 and resulted in near complete lysis at 24 hr. The amount of degradation with MMP-3 (1:20) at 24 hrs was comparable to that produced by plasmin (1:1200). Therefore, MMP-3 is a slower fibrinolytic enzyme than plasmin. The rates of clot solubilization with MMP-1 and MMP-2 were much slower: at the same E:S ratio (1:20), only 34% and 58% respectively, was solubilized after 24 hr, whereas 84% was degraded by MMP-3. In digests with MMP-3 and plasmin, residual clot radioactivity was ≦10%. These results indicated that digestion of XL-Fb with MMP-3 progressed further, possibly with a different and more specific mechanism than that obtained with either MMP-1 or MMP-2. However, the weaker activity of MMP-2 may be due to rapid autolysis of the enzyme after activation by APMA (Okada et al. 1990).

EXAMPLE 5

MMP-3-Induced Cleavage of γ-Chain Cross-Link Domain. Immunoblots performed using standard techniques were performed on plasmin and metalloproteinase digests of fibrin with a panel of monoclonal antibodies (MoAbs) (see Table II) to identify how the three chains of fibrin are cleaved by MMP-3 in comparison with plasmin. Monoclonal antibodies were prepared according to techniques known in the art.

TABLE II

MONOCLONAL ANTIBODIES

| Antibody | Isotype | Cross-Reacts With |
|---|---|---|
| MoAb/4A5 (Gift) | IgGl,k | γ397–311, native fibrinogen and fragments D/D-dimer Matsueda et al. 1988) |
| MoAb/4-2 | IgGl,k | γ392–406, fibrinogen and fragments D/D-dimer but only after denaturation (Kudryk et al. 1991) |
| MoAb/T2G1 | IgGl,k | Bβ15–42, fibrin II, but not fibrinogen/fibrin I (Kudryk et al. 1984) |
| MoAb/1D4 | IgGl,k | Aα349–406, fibrinogen, fibrin, and plasmin digests of both (Procyk et al. 1991) |

Samples were incubated either with or without enzyme for 24 or 48 hr. Incubated samples were then subjected to SDS-PAGE (7% gels) under reducing conditions. After electrophoresis, samples were transferred to nitrocellulose membranes, and the membranes were blotted with selected antibodies. Specific antibody-bound fibrin(ogen) chains were detected using RAM-HRPO and the chemiluminescent substrate, as described above. The results are illustrated in FIGS. 4–5.

Figure 4A:
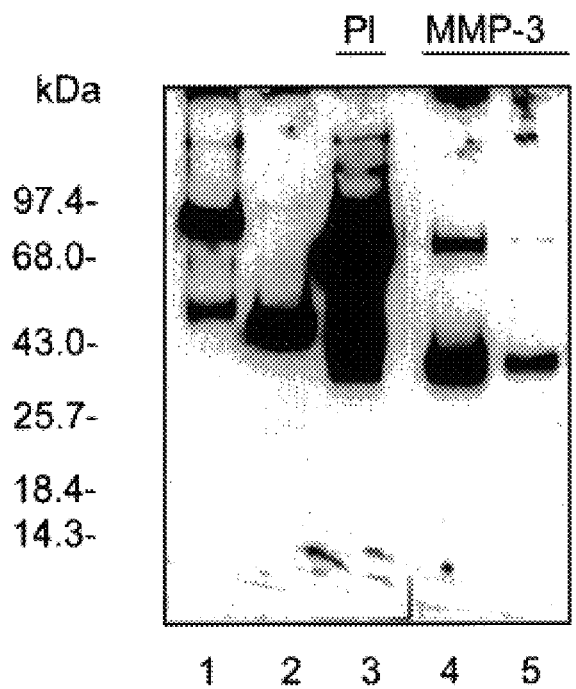
FIG. 4A shows an immunoblot of the degradation products of fibrin digestion by MMP-3 and plasmin, as measured with MoAb/4-5 (γ392-406).
Figure 5:
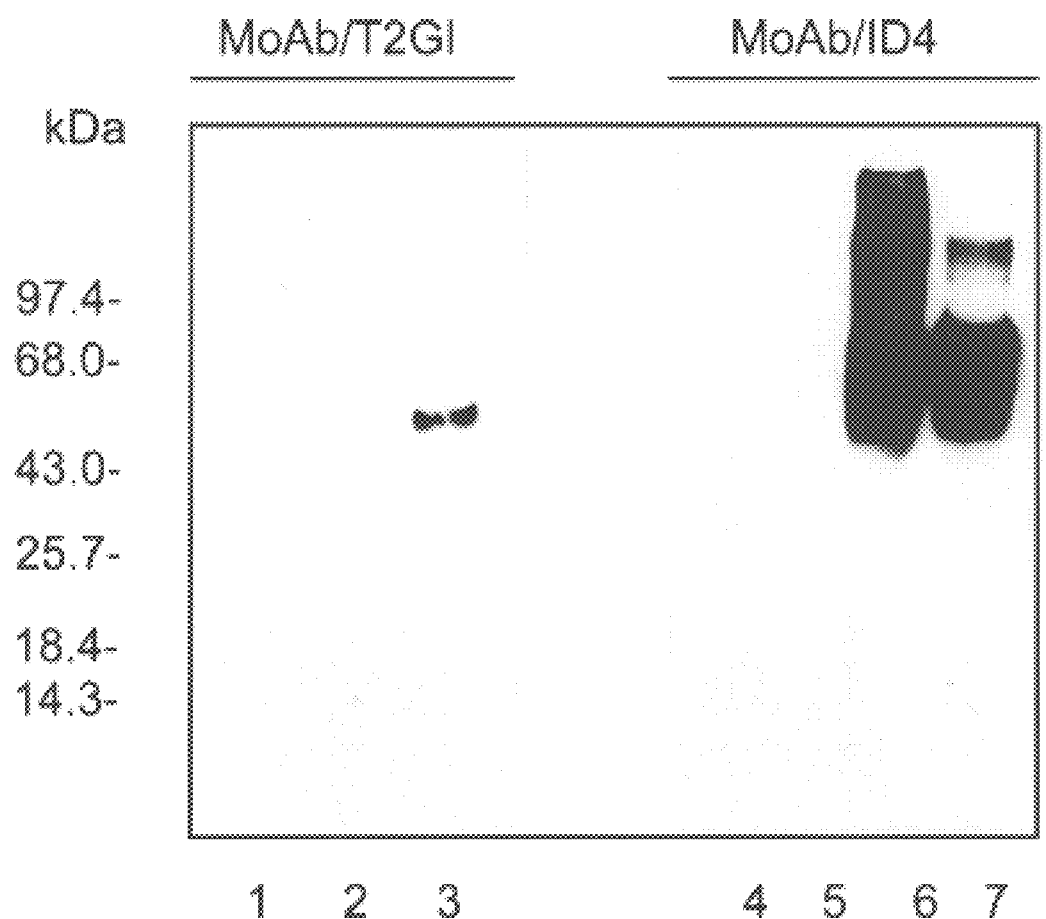
FIG. 5 shows an immunoblot of the degradation products of fibrin digestion by MMP-3, as measured with MoAb/T2G1 (Bβ15-42) and MoAb/1D4 (Aα349-406).

FIG. 4A shows immunoblots of the degradation products of fibrin digestion by MMP-3 and plasmin with MoAb/4-2. This antibody is specific to an epitope in the γ-chain: γ392-406. This antibody reacts with fibrinogen and the D and D-dimer fragments only after denaturation.

Cross-linked fibrin and fibrinogen were each incubated without enzyme at 37° C., for 24 hr. Also, XL-Fb was incubated with plasmin (24 hr) and with MMP-3 (24 hr and 48 hr) The digests were examined under reducing conditions. The key to FIG. 4A is as follows:

| Lane No. | Sample |
|---|---|
| 1 | XL-Fb |
| 2 | Fg |
| 3 | Plasmin digest of XL-Fb (24 hr) |
| 4 | MMP-3 (1:20) digest of XL-Fb, residual clot (24 hr) |
| 5 | MMP-3 (1:20) digest of XL-Fb, total digest (48 hr) |

As seen in FIG. 4A, MoAb/4-2 (anti-γ392-406) reacted with both undigested XL-Fb γ-dimer (94 kDa, lane 1) and undigested Fg γ-chain (47 kDa, lane 2). Residual γ-chain monomer in the cross-linked fibrin preparation also reacted with MoAb/4-2 (lane 1). In the plasmin digest of XL-Fb, DD γ-dimer (76 kDa) and Fragment D γ-chain monomer (known to result from both Fg and XL-Fb plasmin digests (Siebenlist et al. 1992)) also reacted equally with MoAb/4-2 (lane 3). A 24 hr digest of XL-Fb generated by MMP-3 showed reduced DD γ-dimer chain in the residual clot, but significant amounts of Fragment D monomer-like γ-chain (36 kDa, lane 4). A longer incubation (48 hr) showed only Fragment D monomer-like γ-chain in the total digest. Digests with both enzymes bound MoAb/4-2.

Figure 4B:
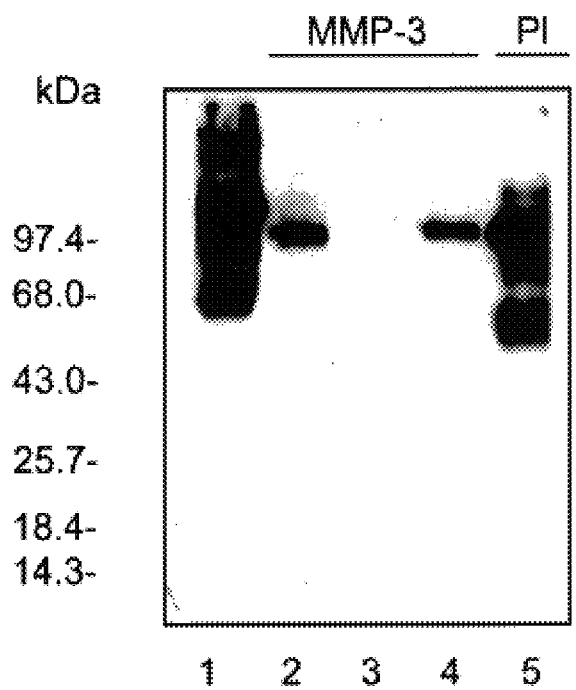
FIG. 4B shows an immunoblot of the degradation products of fibrin digestion by MMP-3 and plasmin, as measured with MoAb/45 (γ397-411).

Cross-inked fibrin was also examined by immunoblotting with MoAb/4A5, which is specific for the γ-chain at γ397-411, an epitope close to that reactive with MoAb/4-2. As a benchmark, XL-Fb clot was incubated without enzyme at 37° C. for 48 hr. XL-Fb was also incubated with MMP-3 or plasmin for 24 hr. The results of this immunoblot are shown in FIG. 4B. The key to FIG. 4B is as follows:

| Lane No. | Sample |
|---|---|
| 1 | Undigested XL-Fb clot |
| 2 | MMP-3 (1:20) digest of XL-Fb, residual clot (24 hr) |
| 3 | MMP-3 (1:20) digest of XL-Fb, clot supernatant (24 hr) |
| 4 | MMP-3 (1:20) digest of XL-Fb, total digest (24 hr) |
| 5 | Plasmin digest of XL-Fb |

Thus, as seen in FIG. 4B, MoAb/4A5 (anti-γ397-411) showed reactivity only with the γ-dimer band from both intact and plasmin-digested XL-Fb (lanes 1, 5) and with residual DD γ-dimer from digests generated by MMP-3 (lanes 2, 4). The Fragment D monomer-like γ-chain (36 kDa), fully reactive with MoAb/4-2 (FIG. 4A, lanes 4, 5) failed to bind MoAb/4A5 (FIG. 4B, lanes 2, 4). Immunoblot analysis of the same samples under non-reducing conditions showed similar loss of immunoreactivity with MoAb/4A5 (data not shown).

These experiments show that the pattern of XL-Fb degradation with MMP-3 is different from that obtained with plasmin. In digests with MMP-3 (1:20), only very small amounts of γ-dimer remain. At higher levels of this same enzyme, no dimers can be detected. MMP-2 does not seem to affect the degradation of γ-dimer significantly. Two monoclonal antibodies, MoAb/4-2 and MoAb/4A5, reactive with different epitopes in the sequence γ392-411, were used to define the regions of cleavage of XL-Fb by MMP-3 in comparison to plasmin. This segment of the chain contains residues (γGln398 and γLys406) that participate in covalent cross-linking (forming ε-(γ-Glu)-Lys isopeptide bonds) on neighboring molecules leading to fibrin stabilization mediated by Factor XIIIa (Chen et al. 1971). MoAb/4A5 recognizes an epitope in the COOH-terminal region of this peptide (γ397-411), while MoAb/4-2 reacts with its NH$_2$-terminal end (γ392-406). Both antibodies bind to microtiter plates coated with the plasmin-derived digest products Fragments D and DD. Only MoAb/4A5 competes with such fragments when each is in solution (Kudryk et al. 1991). In a 24 hr MMP-3-digest of XL-Fb, both residual DD γ-dimer chain and Fragment D monomer-like γ-chain were reactive with MoAb/4-2. Longer (48 hr) digests resulted in Fragment D monomer-like γ-chain only, which was still reactive with MoAb/4-2. Analysis of these same digests with MoAb/4A5 (anti-γ397-411) showed only the DD γ-dimer band to be reactive. The Fragment D monomer-like γ-chain failed to bind MoAb/4A5. These results suggested that a major MMP-3 cleavage site was within the γ-chain cross-link domain resulting in the degradation of the γ-dimer. Purified Fragment DD, was also cleaved with MMP-3 to a D-monomer like fragment.

Immunoblot of the degradation products of fibrin digestion by MMP-3 and plasmin was also performed using MoAb/T2G1 and MoAb/1D4 under reducing conditions, as shown in FIG. 5. The experimental protocol was as described above for the other antibodies. The key to FIG. 5 is as follows:

| Lane No. | Sample |
|---|---|
| 1 | MMP-3 (1:200) digest of XL-Fb (24 hr) |
| 2 | MMP-3 (1:20) digest of XL-Fb (24 hr) |
| 3 | Undigested XL-Fb (24 hr) |
| 4 | MMP-3 (1:200) digest of XL-Fb (24 hr) |
| 5 | MMP-3 (1:20) digest of XL-Fb (24 hr) |
| 6 | Undigested XL-Fb (24 hr) |
| 7 | Undigested Fg (24 hr) |

As indicated in FIG. 5, lanes 1–3 were blotted with MoAb/T2G1, while lanes 4–7 were blotted with MoAb/1D4.

MoAb/T2G1 is specific for Bβ15-42, but only of fibrin II, not of fibrinogen/fibrin I.

MoAb1D4 is specific for Aα349-406 in fibrinogen and fibrin, as well as in their plasmin digests. As shown in FIG. 5, MoAb/T2G1 immunoreactivity was lost in the digests of fibrin by MMP-3 both at lower (1:200) and higher (1:20) concentration (lanes 4, 5), while it is present in intact fibrin (lane 6). MoAb1D4 immunoreactivity is still partially preserved in the fibrin digest at lower concentration of MMP-3 (lane 1), but it is completely lost in digests at higher concentration of MMP-3 at both 24 hr (lane 2) and 48 hours (not shown), while it is clearly present in the control sample (lane 3).

Accordingly, MMP-3 degradation products of XL-Fb were probed with MoAbs, T2G1 (anti-Bβ52-42) and 1D4 (anti-Aα349-406), respectively. Both epitopes are present in XL-Fb. In plasmin digests of XL-Fb, many different size bands (≧20 kDa) react with MoAb/1D4, while all MoAb/T2G1 reactivity is lost. Even relatively low concentrations of MMP-3 (1:200) resulted in digests which failed to react with these antibodies on immunoblotting. This result means that Aα349-406 has been cleaved from fibrin by MMP-3. No immunoreactivity with MoAb/1D4 in MMP-3-digests of XL-Fb could be detected by competition ELISA. This antibody reacts identically with Aα349-406 and Hi2-DSK (Aα241-476) before and after complete digestion with trypsin.

EXAMPLE 6

Figure 6A:
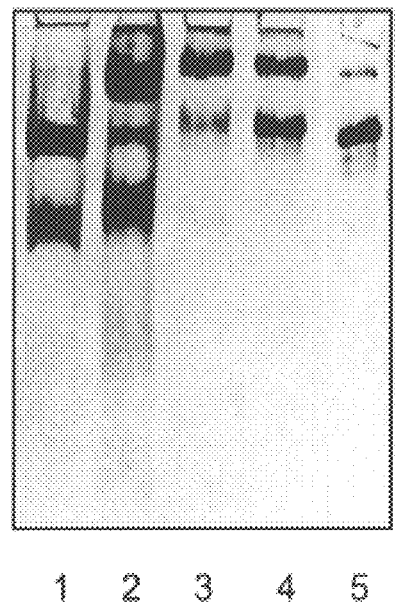
FIG. 6A shows an electrophoretic analysis (non-reducing conditions) of D-dimer treated with MMP-3, showing time- and concentration-dependent degradation of D-dimer by MMP-3.
Figure 6B:
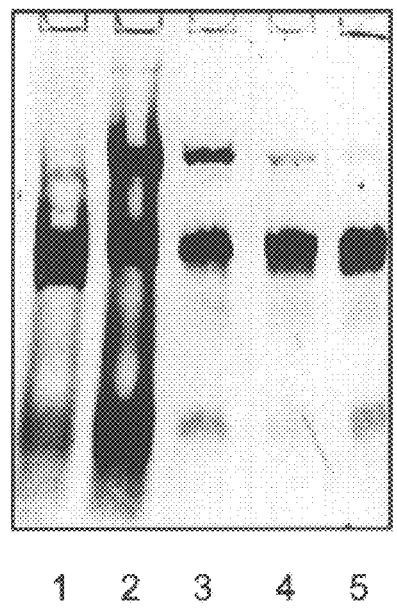
FIG. 6B shows an electrophoretic analysis (reducing conditions) of D-dimer treated with MMP-3, showing time- and concentration-dependent degradation of D-dimer by MMP-3.

Digestion of Fragment D-Dimer (DD) by MMP-3. Experiments were carried out to see whether MMP-3 would cleave purified D-dimer (DD) into D monomer. Purified fragment D and D-dimer were incubated 37° C. for 4 and 24 hours with lower (1:20) and higher (1:200) concentration of MMP-3. The reactions were terminated with 25 mM EDTA. The digests were resolved on PAGE (7% phosphate). The samples were transferred to nitrocellulose membranes and stained with Coomassie blue. The results are shown in FIG. 6. Samples were run under non-reducing (FIG. 6A) and reducing (FIG. 6B) conditions. The key to FIGS. 6A and 6B is as follows:

| Lane No. | Sample |
|---|---|
| 1 | Plasmin digested Fg (D monomer 93 kDa) |
| 2 | Plasmin digested XL-Fb (D dimer 186 kDa) |
| 3 | MMP-3 digest (1:200) of purified D dimer (4 hr) |
| 4 | MMP-3 digest (1:20) of purified D dimer (4 hr) |
| 5 | MMP-3 digest (1:20) of purified D dimer (24 hr) |

As shown in FIGS. 6A and 6B, progressive (time-dependent) degradation of D dimer (186 kDa) into D monomer-like fragment (lanes 4, 5). The size of the resulting monomer was slightly larger than Fragment D (93 kDa), obtained during plasmin degradation of Fg (lane 1). Also, as this gel was made 2 months after preparation of these samples, this proves that the reaction has been stopped effectively and has not progressed any further. The results indicate that monomerization occur even at 4 hours with the lower amount of enzyme (1:200) (lane 3). Increasing the amount of enzyme ten-fold increases the monomerization at 4 hours (lane 4) and almost completely converts the substrate at 24 hours (lane 5). This is supported in FIG. 6B, which shows the conversion of γ dimer (78 kDa) to γ monomer-like chain (38 kDa).

EXAMPLE 7

Analysis of MMP Digestion Products by ELISA. ELISA binding assays were performed using generally accepted methods. Polyvinyl microtiter plates were coated with appropriate dilutions of different digests and assayed for antibody binding (Kudryk et al. 1984). In accord with the results shown in FIG. 4, digests with increasing concentrations of MMP-3 failed to bind MoAb/4A5 (anti-γ397-411). This means that the fibrinogen cleavage site of MMP-3 is in the region of this epitope (the fibrin cross-links occur in the region γGly397-Lys406). This type of cleavage does not occur with plasmin. However, the digests were found to be reactive with MoAb/4-2 (γ349-406). No immunoreactivity with MoAb/1D4 in MMP-3 digests of XL-Fb could be detected by competition ELISA, suggesting that the 1D4-reactive epitope is destroyed in such digests. MoAb/1D4 binds equally to plasmin digests of Fg and XL-Fb.

Thus, the ELISA (direct binding) performed on digests of Fg and XL-Fb with MMP-3 showed that the linear sequence epitope γ392-406 (MoAb/4-2-reactive), but not γ397-411 (MoAb/4A5-reactive), could be detected by this method. This confirmed the results obtained with immunoblotting and further suggested that MMP-3 cleaves within the sequence γ397-411. NH$_2$-terminal sequence analysis of the dipeptide (isolated from CNBr degradation of XL-fibrin digested with MMP-3) indicated that γAla405 is the first residue of the second sequence (See Examples 8–9, below). We note that MoAb/4-2 also binds a synthetic peptide whose sequence corresponds to γ392-400. MoAb/4A5 reacts with synthetic peptides corresponding to γ392-411 and γ397-411, which is lost when either peptide is cleaved with trypsin at γLys406-Gln407. This feature is consistent with the observed lack of reactivity of MoAb/4A5 with the dipeptide.

EXAMPLE 8

Size and Sequence Analysis of Chains of MMP-3-Digested Fg and XL-Fb. Fg and XL-Fb digested with MMP-3 were separated under reducing conditions on a 12.5% SDS-PAGE (Laemmli 1970) and electroblotted to a polyvinylidene difluoride membrane (PVDF) (Matsudaira 1987). The portion of the membrane that contained the γ-chain fragment was excised and subjected to automated sequencing on a model 477A Applied Biosystems Inc. pulsed liquid phase sequencer with a model 120A on-line phenylthiohydantoin (PTH) amino acid analyzer.

The digests of both Fg and XL-Fb yielded a γ-chain sequence Leu-Lys-Ser-Arg-Lys (SEQ ID NO:1), indicating that MMP-3 cleaves both Fg and XL-Fb at the γThr83-Leu84 bond. This same band from the XL-Fb digest, however, also gave a second γ-chain sequence Ala-X-Gln-Ala-Gly-Asp (SEQ ID NO:2) indicating MMP-3-induced hydrolysis at the γGly404-Ala405 bond, in the γ-chain cross-link region.

EXAMPLE 9

Characterization of a CNBr-derived γ-chain fragment from MMP-3 digests of XL-Fb. To confirm the results obtained from sequencing the γ-chain of XL-Fb degraded with MMP-3, the same digest was treated with CNBr (Blombäck et al. 1968) and the fragment reactive with MoAb/4-2 (anti-γ392-406) was isolated, as follows. MMP-3-cleaved fragments were purified by reverse-phase HPLC using a Vydac C-4 column (1.0×25 cm, The Sep/a/ra/tions Group, Hesperia, Calif.). The column was developed at room temperature using the following gradient constructed with 0.05% trifluoroacetic acid (TFA, solvent A) and 50% acetonitrile in A (solvent B): at 5% B/0.5 min; 5 to 50% B/at 50 min; 50 to 100% B/at 70 min; 100% B/at 75 min. Column flow rate was 1.0 mL/min and fractions (1 mL) were monitored for reactivity with MoAb/4-2 (anti-γ392-406). The antibody-reactive fraction was further purified by FPLC using the Superdex Peptide HR 10/30 column (1.0×30–31 cm, Pharmacia Biotech, Piscataway, N.J.). The column was developed at room temperature using 20 mM phosphate buffer (pH 7.2), additionally containing 0.25M NaCl. The fraction reacting with MoAb/4-2 was pooled, desalted by passage over Sep-Pak® (Millipore Corp., Milford, Mass.) and subjected to sequence analysis.

Figure 7:
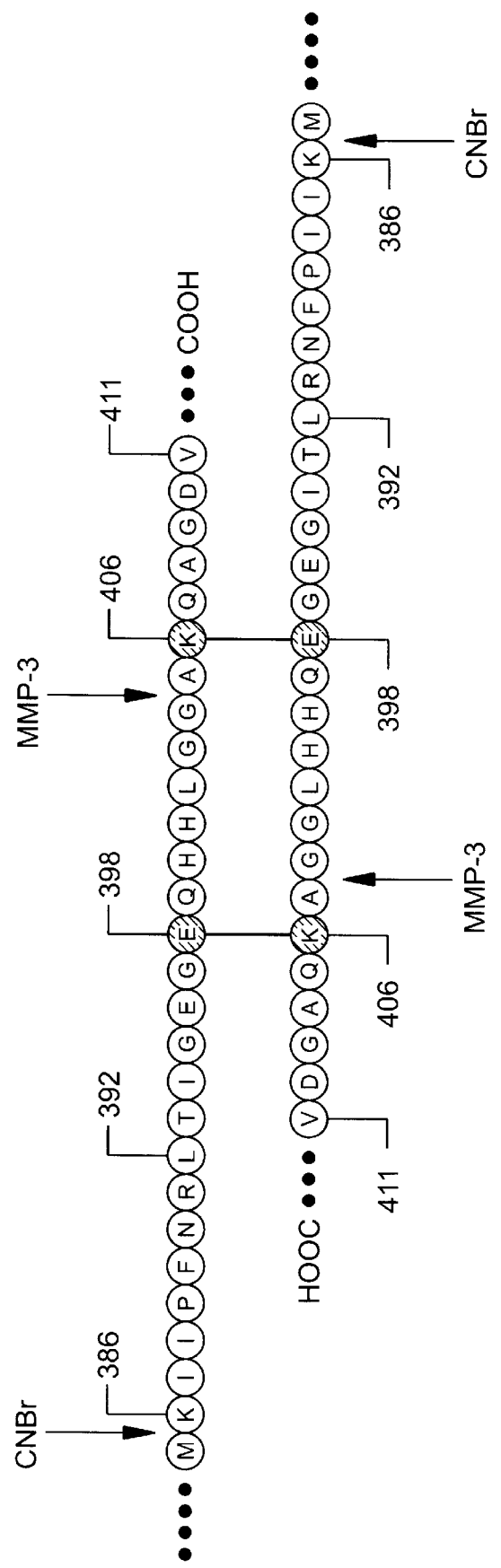
FIG. 7 is a schematic diagram illustrating the cross-linking region in cross-linked fibrin, showing cleavage sites of MMP-3 and CNBr (i.e., SEQ ID NO:6 SEQ ID NO:7).

The sequenced fragment corresponded to a cross-linked dipeptide with two distinct NH$_2$-terminals: γLys385, resulting from CNBr cleavage, and γAla405 (FIG. 7). The two sequences were recovered in comparable molar quantities. In cycle 3 NH$_2$-terminal analyses showed no PTH residues (due to a machine error), but evidence for Gln and Ile in cycle 3 was seen in cycle 4 as lag. These data support our conclusion that MMP-3 cleaves at γGly404-Ala405 within the cross-link region of fibrin γ-chain.

Table III shows the partial sequence for the cross-linked dipeptide isolated from XL-Fb digested with MMP-3 after CNBr degradation. The γ cross-linking domain, with the sites of MMP-3 digestion and CNBr cleavage, is shown schematically in FIG. 7. The resulting dipeptide contains a single ε-(γ-Glu)-Lys bond, with one NH$_2$-terminal as γLys385, resulting from CNBr cleavage at γMet384-Lys385. The presence of the second NH$_2$-terminal, γAla405, supported our conclusion that MMP-3 cleaves at γGly404-Ala405 in the cross-link region of the γ-chain.

TABLE III

| Cycle | PTH Amino Acid/Yield (pmol) | |
|---|---|---|
| 1 | K (215) | A (673) |
| 2 | I (648) | — |
| 3 | I* | Q* |
| 4 | P (406) | A (438) |
| 5 | F (352) | G (565) |
| 6 | N (219) | D (202) |
| 7 | R (200) | V (115) |
| 8 | L (313) | — |
| 9 | T (179) | — |
| 10 | I (349) | — |

Data obtained from sequence analysis of MMP-3 digests of Fg and XL-Fb showed proximity of cleavage sites with plasmin on these same substrates. Plasmin cleaves at γLys62-Ala63 and more slowly at γLys85-Ser86 (Collen et al. 1975). Thus, fibrinogen digested by plasmin results in two Fragment D species, i.e., γAla63-Val411 and γSer86-Val411. By contrast, MMP-3 cleaves both Fg and XL-Fb at γThr83-Leu84. In addition, since MMP-3 hydrolyzes the γGly404-Ala405 peptide bond, the γ-chain has a molecular weight which is substantially similar to that of plasmin-generated Fragment D γ-chain. However, in the digests of XL-Fb with MMP-3, this product is not a real monomer since the γ405-411 domain is cross-linked to the adjacent γ-chain having the sequence γLeu84-Gly404. It should be noted that the recovery of similar quantities of the two sequences from the γ-chains of the CNBr-generated dipeptide indicated that, albeit slow, the degradation of XL-Fb by MMP-3, resulting in formation of the D monomer-like fragment, was near complete.

EXAMPLE 10

Figure 8:
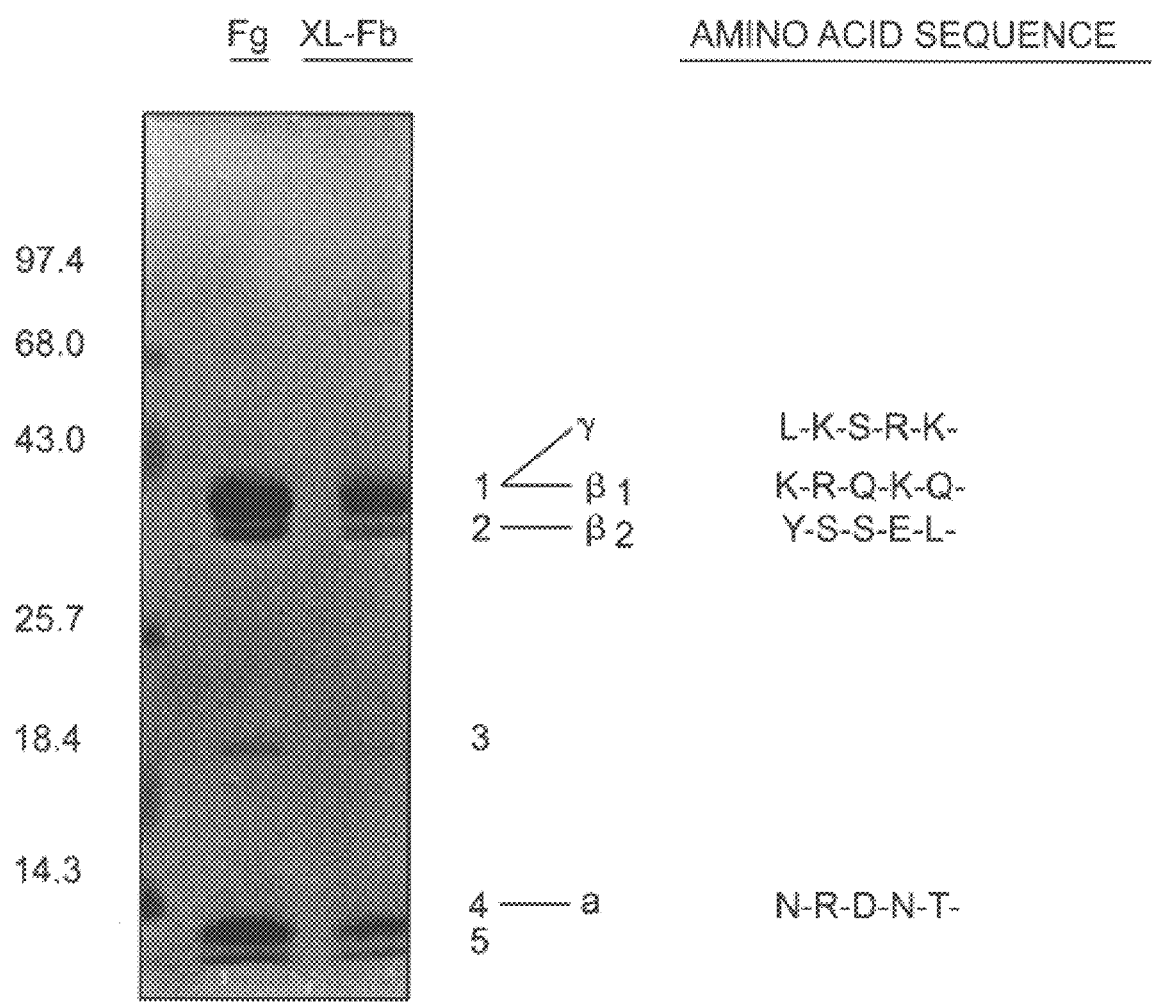
FIG. 8 shows an electrophoretic analysis of the products of degradation of fibrinogen and cross-linked fibrin by MMP-3.

Characterization of Other Cleavage Products of Fg and XL-Fb by MMP-3. MMP-3 also generates other cleavage products of Fg and XL-Fb, specifically cutting not only the γ-chain, but also the α- and β-chains. Fg and XL-Fb were digested using MMP-3 (E:S=1:20) for 24 hr, separated, and sequenced using the methods described in Example 9. As indicated in FIG. 8, both Fg (lane 1) and XL-Fb (lane 2) were specifically cleaved. In FIG. 8, band 1 was found to include two fragments: a γ-chain fragment having an $NH_2$-terminal sequence of Leu-Lys-Ser-Arg-Lys (SEQ ID NO:1), again corresponding to cleavage γ84; and a β-chain fragment ($β_1$) having an $NH_2$-terminal sequence Lys-Arg-Gln-Lys-Gln (SEQ ID NO:3) corresponding to cleavage at β127. Band 2 was found to contain another β-chain fragment ($β_2$) having the $NH_2$-terminal sequence Tyr-Ser-Ser-Glu-Leu (SEQ ID NO:4), corresponding to cleavage at β142. Band 3 is the enzyme MMP-3 remaining in the digest preparation. Band 4 was found to contain an α-chain fragment having an $NH_2$-terminal sequence Asn-Arg-Asp-Asn-Thr (SEQ ID NO:5), corresponding to cleavage at α103. (Band 4 was also found to contain fragments cleaved at γ1 and α414 in both fibrinogen and fibrin digests.) Band 5 contained fragments cleaved at β51 and β52 in both fibrin and fibrinogen digests with MMP-3.

Accordingly, the evidence presented in Examples 1–10, above, establishes that fibrinogen becomes thrombin-unclottable when treated with matrix metalloproteinase 3 (MMP-3, stromelysin 1), but not when treated with matrix metalloproteinase 2 (MMP-2, gelatinase A). Incubation of XL-Fb clots (made with $^{125}$I-Fg) with MMP-3 results in complete lysis after 24 hrs. A D monomer-like fragment is generated by MMP-3 degradation of fibrinogen, XL-Fb and Fragment DD. Immunoreactivity with monoclonal antibody MoAb/4-2 (anti-γ392-406), but not with MoAb/4A5 (anti-γ397-411), suggested that a major cleavage site was within the sequence participating in the cross-linking of two γ-chains. $NH_2$-terminal sequence of the γ-chain of the D monomer-like fragment and of a dipeptide isolated from the MMP-3 digest of XL-fibrin, identified the hydrolysis of γGly404-Ala405 peptide bond. These data indicate that the degradation of Fg and XL-Fb by MMP-3 is specific and different from plasmin. This mechanism of fibrinolysis is of relevance in wound healing, inflammation, atherosclerosis, malignancy, renal disease, and other pathophysiological processes.

Inasmuch as MMP-3 cleaves near the site at which fibrin cross-linking occurs, a strong teleological argument is readily made that MMP-3 plays a singular role in fibrinolysis. Coordinated regulation of the metalloproteinases and plasminogen activators could, therefore, result in synergistic effects and complete degradation of both the extracellular matrix and the fibrin meshwork resulting from wound healing, inflammation, thrombosis, cancer, renal disease, or other pathophysiological processes. Accordingly, it is contemplated that the co-administration of MMP-3 with another thrombolytic agent such as t-PA would also achieve an adjunctive therapeutic effect, in which each component complements or potentiates the other.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

Bilezikian, S. B., and Nossel, H. L., *Blood* 50:21–28 (1977).

Bini, A., Fenoglio, J. J., Jr., Sobel, J., Owen, J., Fejgl, M., and Kaplan K. L., *Blood* 69:1038–1045 (1987).

Bini, A., Fenoglio, J. J., Jr., Mesa-Tejada, R., Kudryk, B., and Kaplan, K. L., *Arteriosclerosis* 9:109–121 (1989).

Bini A., Callender S., Pocyk R., Blombäck B., and Kudryk B. J., "Flow and antibody binding properties of hydrated fibrins prepared from plasma, platelet rich plasma and whole blood", *Thrombosis Res* 76:145–56 (1994).

Blombäck, B., Blombäck, M., Henschen, A., Hessel, B., Iwanaga, S., and Woods, K. R., *Nature* 218:130–134 (1968).

Blombäck, B., and Okada, M., *Thromb Res* 25:51–70 (1982).

Blombäck, B., Carlsson, K., Fatah, K., Hessel, B., and Procyk, R., *Thromb Res* 75:521–538 (1994).

Brakman P., and Kluft C., eds., Plasminogen Activation in Fibrinolysis, in Tissue Remodeling, and in Development, *Ann NY Acad Sci*, vol. 667 (1992).

Budzynski A. Z., "Interaction of hementin with fibrinogen and fibrin", *Blood Coagulation and Fibrinolysis* 2:149–52 (1991).

Campbell, E. J., Cury, J. D., Shapiro, S. D., Goldberg, G. I., and Welgus, H. G., *J Immunol* 146:1286–1293 (1991).

Cawston T., "Metalloproteinase inhibitors—Crystal gazing for a future therapy", *Br J Rheumatol* 30:242–44 (1991).

Chen, R., and Doolittle, R. F., *Biochemistry* 10:4486–4491 (1971).

Collen, D., Kudryk, B., Hessel, B., and Blombäck, B., *J Biol Chem* 250:5808–5817 (1975).

Collen D., "On the regulation and control of fibrinolysis", *Thromb Haemost* 43:77–89 (1980).

Collen D., "Biological properties of plasminogen activators", Chapter 1 in Sobel B. E., Collen D., and Grossbard E. B., eds., *Tissue Plasminogen Activator in Thrombolytic Therapy*, Marcel Dekker, Inc., New York (1987).

Collen D., and Lijnen H. R., "Basic and clinical aspects of fibrinolysis and thrombolysis", *Blood* 3114–24 (1991).

Collen D., "Fibrin-selective thrombolytic therapy for acute myocardial infarction", *Circulation* 93:857–865 (1996).

Deutsch, D. G., and Mertz, E. T., *Science* 170:1095–1096 (1970).

Doolittle R. F., "Fibrinogen and fibrin", in Bloom A. L., and Thomas D. P., eds., *Hemostasis and Thrombosis* Churchill Livingston, Edinburgh, N.Y. (1987).

Engvall, E., and Ruoslahti, E., *Int J Cancer* 20:1–5 (1977).

Francis C. W., and Marder V. J., "Physiologic regulation and pathologic disorders of fibrinolysis", Chapter 54 in *Hemostasis and Thrombosis: Basic Principles and Clinical Practice*, 3rd ed., Colman R. W., Hirsh J., Marder V. J., and Salzman E. W., eds., J. B. Lippincott Co, Philadelphia (1994).

Fu Y., and Grieninger G., "$Fib_{420}$: A normal human variant of fibrinogen with two extended α chains", *Proc Natl Acad Sci USA* 91:2625–28 (1994).

Gabriel D. A., Muga K., and Boothroyd E. M., "The effect of fibrin structure on fibrinolysis", *J Biol Chem* 267:24259–63 (1992).

Galis Z. S., Sukhova G. K., Lark M. W., and Libby P., "Increased expression of matrix metalloproteinases and matrix degrading activity in vulnerable regions of human atherosclerotic plaques", *J Clin Invest* 94:2493–2503 (1994).

Galis, Z. S., Sukhova, G. K., Kranzhofer, R., and Libby, P., *Proc Natl Acad Sci USA* 92:402–406 (1995).

Gårdlund, B., Kowalska-Loth, B., Gröndahl, N. J., and Blombäck, B., *Thromb Res* 1:371 (1972).

Glick B. R., and Pasternak J. J., *Molecular Biotechnology: Principles and Applications of Recombinant DNA*, Chapter 17, pp. 403–20 (1994).

Goding, J. W., in *Monoclonal Antibodies: Principles and Practice*, Academic Press, New York, N.Y, (1986).

Gramse, M., Bingenheimer, C., and Schmidt, W., *J Clin Invest* 61:1027–1033 (1978).

Guan, A. L., Retzios, D., Henderson, G. N., and Markland, F. S., *Arch Biochem Biophys* 289:197–207 (1991).

Henney A. M., Wakeley P. R., Davies M. J., Foster K., Hembry R., Murphy G., and Humphries S., "Localization of stromelysin gene expression in atherosclerotic plaques by in situ hybridization", *Proc Natl Acad Sci USA* 88:8154–58 (1991).

Kleiner D. E. Jr., and Stetler-Stevenson W. G., "Structural biochemistry and activation of matrix metalloproteinases", *Curr Opin Cell Biol* 5:891–97 (1993).

Kudryk, B., Rohoza, A, Ahadi, M., Chin, J., and Wiebe, M. E., *Mol Immunol* 21:89–94 (1984).

Kudryk B. J., Grossman Z. D., McAfee J. G., and Rosebrough S. F., "Monoclonal antibodies as probes for fibrin (ogen) proteolysis", Chapter 19 in *Monoclonal Antibodies in Immunoscintigraphy*, Chatal J.-F., ed., CRC Press, Boca Raton (1989a).

Kudryk, B., Gidlund, M., Rohoza, A, Ahadi, M., Coiffe, D., and Weitz, J. I., *Blood* 74:1036–1044 (1989b).

Kudryk, B., Rohoza, A, Ahadi, M., Gidlund, M., Procyk, R., and Matsueda, G. R., *Thromb Haemostas* 65:898 (Abstract 714) (1991).

Laemmli, V. K., *Nature* 227:680–685 (1970).

Laemmli U. K., and Favre M., "Maturation of the head of bacteriophage T4. I. DNA packaging events", *J Mol Biol* 80:575–99 (1973).

Lee S. W., Kahn M. L., and Dichek D. A., "Control of clot lysis by gene transfer", *Trends Cardiovasc Med* 3:61–66 (1993).

Liu, C. Y., Sobel, J. H., Weitz, J. I., Kaplan, K. L., and Nossel, H. L., *Thromb Haemostas* 56:100–106 (1986)

Loewy A. G., Santer U. V., Wieczorek M., Blodgett J. K., Jones S. W., and Cheronis J. C., "Purification and characterization of a novel zinc-proteinase from cultures of *Aeromonas hydrophila*", *J Biol Chem* 268:9071–78 (1993).

Martin G. V., Kennedy J. W., and Marder V. J., "Thrombolytic therapy for coronary artery disease", Chapter 73 in *Hemostasis and Thrombosis: Basic Principles and Clinical Practice*, 3rd ed., Colman R. W., Hirsh J., Marder V. J., and Salzman E. W., eds., J. B. Lippincott Co, Philadelphia (1994).

Matrisian L. M., "The matrix-degrading metalloproteinases", *BioEssays* 14:455–63 (1992).

Matsudaira, P., *J Biol Chem* 262:10035–10038 (1987).

Matsueda G. R., and Bernatowicz M. S., (1988) in *Fibrinogen 3-Biochemistry, Biological Functions, Gene Regulation and Expression* (Mosesson M. W., Amrani D., Siebenlist K. R., DiOrio P. Eds) pp 133–136 Elsevier Science Publishers B. V., Amsterdam.

McDonagh J., Messel H., McDonagh R. P., Jr., Murano G., and Blomback B., "Molecular weight analysis of fibrinogen and fibrin chains by an improved sodium dodecyl sulfate gel electrophoresis method", *Biochim Biophys Acta* 257:135–42 (1972).

Murphy G., Atkinson S., Ward R., Gavrilovic J., and Reynolds J. J., "The role of plasminogen activators in the regulation of connective tissue metalloproteinases", *Ann NY Acad Sci*, 667:1–12 (1992).

Nagase H., Enghild J. J., Suzuki K., and Salvesen G., "Stepwise activation mechanisms of the precursor of matrix metalloproteinase 3 (stromelysin) by proteases and (4-aminophenyl)mercuric acetate", *Biochemistry* 29:5783–89 (1990).

Nagase H., Ogota Y., Suzuki K., Enghild J. J., and Salvesen G., "Substrate specificities and activation mechanisms of matrix metalloproteinases", *Biochem Soc Trans* 19:715–18 (1991).

Nagase H., Barrett A. J., and Woessner J. F. Jr., "Nomenclature and glossary of the matrix metalloproteinases", *Matrix Supplement* 1:421–24 (1992).

Okada Y., Nagase H., and Harris E. D., Jr., "A metalloproteinase from human rheumatoid synovial fibroblasts that digests connective tissue matrix components", *J Biol Chem* 261:14245–55 (1986).

Okada, Y., Morodomi, T., Enghild, J. J., Suzuki, K., Nakanishi, I., Salvesen, G., and Nagase, H., *Eur J Biochem* 194:721–730 (1990).

Plow, E. F., and Edgington, T. S., *J Clin Invest* 56:30–38 (1975).

Plow, E. F., *Biochim Biophys Acta* 630:47–56 (1980).

Plow, E. F., and Edgington, T. S., *Semin Thromb Haemostas* 8:36–56 (1982).

Procyk, R., Adamson, L., Block, M., and Blombäck, B., *Thromb Res* 40:833–852 (1985).

Procyk et al.(1991) *Blood* 77, 1469–1475.

Purves L., Purves M., and Brandt W., "Cleavage of fibrin-derived D-dimer into monomers by endopeptidase from puff adder venom (*Bitis arietans*) acting at cross-linked sites of the γ-chain. Sequence of carboxy-terminal cyanogen bromide γ-chain fragments", *Biochemistry* 26:4640–46 (1987). Retzios A. D., and Markland F. S. Jr., "Purification, characterization, and fibrinogen cleavage sites of three fibrinolytic enzymes from the venom of *Crotalus basiliscus basiliscus*", *Biochemistry* 31:4547–57 (1992).

Sanchez E. F., Magalhes A., Mandelbaum F. E., and Diniz C. R., "Purification and characterization of the hemorrhagic factor II from the venom of the Bushmaster snake (*Lachesis muta muta*)", *Biochim Biophys Acta* 1074:347–56 (1991).

Senior, R. M., Griffin, G. L., Fliszar, J., Shapiro, S. D., Goldberg, G. I., and Welgus, H. G., *J Biol Chem* 266:7870–7875 (1991).

Siebenlist, K. R., and Mosesson, M. W., *Biochemistry* 31:936–941 (1992).

Smith, E. B., Keen, G. A., Grant, A., and Stirk, C., *Arteriosclerosis* 10:263–275 (1990).

Sobel B. E., Collen D., and Grossbard E. B., eds., Tissue Plasminogen Activator in Thrombolytic Therapy, Marcel Dekker, Inc., New York (1987).

Sterrenberg, L., Gravesen, M., Haverkate, F., and Nieuwenhuizen, W., *Thromb Res* 31:719–728 (1983).

Suzuki, K., Nagase, H., Ito, A., Enghild, J. J., and Salvesen, G., *Biol Chem Hoppe-Seyler* 371:305–310 (1990).

Towbin, H., Staehelin, T., and Gordon, J., *Proc Natl Acad Sci USA* 76:4350–4354 (1979).

Welgus, H. G., Campbell, E. J., Cury, J. D., Eisen, A. Z., Senior, R. M., Wilhelm, S. M., and Goldberg, G. I., *J Clin Invest* 86:1496–1502 (1990).

Valenzuela R., Shainoff, J. R., DiBello, P. M., Anderson, J. M., Matsueda G. R., and Kudryk, B. J., *Am J Pathol* 141:861–880 (1992).

Werb, Z., Alexander C. M., and Adler, R. R., *Matrix Supplement* 1:337–343 (1992).

Woessner, J. F., *FASEB J* 5:2145–2154 (1991).

Zavalova L. L., Kuzina E. V., Levina N. B., and Baskova I. P., "Monomerization of fragment DD by destabilase from the medicinal leech does not alter the N-terminal sequence of the γ-chain", *Thrombosis Res* 71:241–44 (1993).

What is claimed is:

1. A method of degrading fibrin(ogen), comprising:
   contacting said fibrin(ogen) with an amount of fibrinolytic matrix metalloproteinase effective for cleaving the fibrin(ogen), wherein said fibrinolytic matrix metalloproteinase cleaves the fibrin(ogen) at the γGly404-Ala405 peptide bond.

2. The method of claim 1, wherein said fibrinolytic matrix metalloproteinase is endogenous to a mammal.

3. The method of claim 1, wherein said fibrinolytic matrix metalloproteinase is a stromelysin.

4. The method of claim 1, wherein said method further comprises:
   contacting said fibrin(ogen) with an effective amount of an adjunct compound having thrombolytic activity.

5. The method of claim 4, wherein said adjunct compound having thrombolytic activity is selected from the group consisting of a plasminogen activator, a hirudin, an enzyme inhibitor, an enzyme, an anticoagulant, an antibody or synthetic peptide specific for platelet gpIIb/IIIa receptor, and a combination thereof.

6. The method of claim 5, wherein said adjunct compound comprises a urokinase-plasminogen activator (u-PA), a tissue-type plasminogen activator (t-PA), streptokinase, staphylokinase, and combinations thereof.

7. The method of claim 1, wherein said method is performed in vivo.

8. A method of fibrinolytic therapy, comprising:
   administering to a subject in need of fibrinolytic therapy a therapeutically effective amount of a fibrinolytic matrix metalloproteinase, wherein said fibrinolytic matrix metalloproteinase cleaves the fibrin(ogen) at the γGly404-Ala405 peptide bond.

9. The method of claim 8, wherein said fibrinolytic matrix metalloproteinase is endogenous to the species of the subject.

10. The method of claim 8, wherein said fibrinolytic matrix metalloproteinase is a stromelysin.

11. The method of claim 8, wherein said method further comprises:
    administering to said subject a therapeutically effective amount of an adjunct compound having thrombolytic activity.

12. The method of claim 11, wherein said adjunct compound having thrombolytic activity is selected from the group consisting of a plasminogen activator, a hirudin, an enzyme inhibitor, an enzyme, an anticoagulant, an antibody or synthetic peptide specific for platelet gpIIb/IIIa receptor, and a combination thereof.

13. The method of claim 12, wherein said adjunct compound comprises a urokinase-plasminogen activator (u-PA), a tissue-type plasminogen activator (t-PA), streptokinase, staphylokinase, and combinations thereof.

14. The method of claim 8, wherein said method is performed following thrombolytic therapy to inhibit vascular reocclusion.

15. The method of claim 8, wherein said method is performed following surgical intervention to inhibit restenosis.

16. The method of claim 8, wherein said method is performed to inhibit initial formation, or promote regression, of atherosclerotic plaques.

17. A composition for thrombolytic therapy, comprising:
    a fibrinolytic matrix metalloproteinase which degrades fibrin(ogen), and a pharmaceutically acceptable carrier, wherein said fibrinolytic matrix metalloproteinase cleaves the fibrin(ogen) at the γGly404-Ala405 peptide bond.

18. The composition of claim 17, wherein said fibrinolytic matrix metalloproteinase is endogenous to a mammal.

19. The composition of claim 17, wherein said fibrinolytic metalloproteinase is a stromelysin.

20. The composition of claim 17, wherein said composition further comprises an adjunct compound having thrombolytic activity.

21. The composition of claim 20, wherein said adjunct compound having thrombolytic activity is selected from the group consisting of a plasminogen activator, a hirudin, an enzyme inhibitor, an enzyme, an anticoagulant, an antibody or synthetic peptide specific for platelet gpIIb/IIIa receptor, and a combination thereof.

22. The composition of claim 21, wherein said, adjunct compound comprises a urokinase-plasminogen activator (u-PA), a tissue-type plasminogen activator (t-PA), streptokinase, staphylokinase, and combinations thereof.

23. A kit for performing thrombolytic therapy comprising:
    a composition comprising a fibrinolytic matrix metalloproteinase, and
    a container, wherein said fibrinolytic matrix metalloproteinase cleaves the fibrin(ogen) at the γGly404-Ala405 peptide bond.

24. The kit of claim 23, wherein said kit further comprises an adjunct compounded having thrombolytic activity, selected from the group consisting of a plasminogen activator, a hirudin, an enzyme inhibitor, an enzyme, an anticoagulant, an antibody or synthetic peptide specific for platelet gpIIb/IIIa, and a combination thereof.

25. The kit of claim 23, further comprising means for administering a therapeutically effective amount of said composition.

26. The kit of claim 25, wherein said administering means includes means for administering said composition parenterally.

27. A method of inhibiting thrombus formation by a medical-related apparatus, comprising:
    contacting a medical-related apparatus with a composition comprising a fibrinolytic matrix metalloproteinase to provide a thrombus-inhibiting surface on said medical-related apparatus.

28. The method of claim 27, wherein said medical-related apparatus is selected from the group consisting of blood collection tubes, culture flasks, test plates, pipets, reagent containers, tubing, membranes, needles, cannulae, catheters, grafts, stents, filters, coils, and valves.

29. A medical-related apparatus having thrombus-inhibiting properties, comprising a medical-related device having provided thereto a thrombus-inhibiting amount of a composition comprising a fibrinolytic matrix metalloproteinase.

30. The apparatus of claim 29, wherein said medical-related apparatus is selected from the group consisting of blood collection tubes, culture flasks, test plates, pipets, reagent containers, tubing, membranes, needles, cannulae, catheters, grafts, stents, filters, coils, and valves.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS:
      (D) TOPOLOGY: linear (ii) MOLECULE TYPE: peptide (iii) HYPOTHETICAL: NO (xi) SEQUENCE DESCRIPTION: SEQ ID NO:1:

Leu Lys Ser Arg Lys
   1            5

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS:
      (D) TOPOLOGY: linear (ii) MOLECULE TYPE: peptide (iii) HYPOTHETICAL: NO (xi) SEQUENCE DESCRIPTION: SEQ ID NO:2:

Ala Xaa Gln Ala Gly Asp
   1            5

(2) INFORMATION FOR SEQ ID NO:3:

(i) SEQUENCE CHARACTERISTICS:

(A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:3:

Lys Arg Gln Lys Gln
    1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:4:

Tyr Ser Ser Glu Leu
    1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:5:

Asn Arg Asp Asn Thr
    1               5

(2) INFORMATION FOR SEQ ID NO:6:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:6:

Met Lys Ile Ile Pro Phe Asn Arg Leu Thr Ile Gly Glu Gly Glu Gln
    1               5                   10                  15

His His Leu Gly Gly Ala Lys Gln Ala Gly Asp Val
                    20                  25

(2) INFORMATION FOR SEQ ID NO:7:

(i) SEQUENCE CHARACTERISTICS:
        (A) LENGTH: 28 amino acids
        (B) TYPE: amino acid
        (C) STRANDEDNESS:
        (D) TOPOLOGY: linear -continued

```
(ii) MOLECULE TYPE: peptide (iii) HYPOTHETICAL: NO (xi) SEQUENCE DESCRIPTION: SEQ ID NO:7:

Val Asp Gly Ala Gln Lys Ala Gly Gly Leu His His Gln Glu Gly Glu
 1               5                  10                  15

Gly Ile Thr Leu Arg Asn Phe Pro Ile Ile Lys Met
             20                  25
```